US005599963A

United States Patent [19]
Carreira et al.

[11] Patent Number: 5,599,963
[45] Date of Patent: Feb. 4, 1997

[54] CATALYSTS FOR PRODUCTION OF β-HYDROXY CARBONYL COMPOUNDS

[75] Inventors: Erick M. Carreira, Pasadena; Robert A. Singer, Los Angeles, both of Calif.

[73] Assignee: California Institute of Technology, Pasadena, Calif.

[21] Appl. No.: 415,237

[22] Filed: Mar. 29, 1995

Related U.S. Application Data

[63] Continuation-in-part of Ser. No. 310,241, Sep. 21, 1994, abandoned.

[51] Int. Cl.$^6$ .................. C07F 7/28; C07F 1/08
[52] U.S. Cl. .................. 556/33; 556/13; 556/19; 556/35; 556/54; 556/55; 556/113; 556/115; 556/116; 556/139; 556/146; 556/148; 556/150; 534/16; 564/170; 564/182; 564/201; 568/55; 568/496; 568/308; 568/414; 560/60
[58] Field of Search .................. 556/13, 19, 33, 556/35, 54, 55, 113, 115, 116, 139, 146, 148, 150; 534/16; 564/170, 182, 201; 568/55, 308, 414, 496; 560/60

[56] References Cited

PUBLICATIONS

Smrĉina, M., et al., "Synthesis of Enantiomerically Pure Binaphthyl Derivatives. Mechanism of the Enantioselective, Oxidative Coupling of Naphthols and Designing a Catalytic Cycle", *J. Org. Chem.*, 58:4534–4538 (1993).

Sasai, H., et al., "Catalytic Asymmetric Nitroaldol Reactions. A New Practical Method for the Preparation of the Optically Active Lanthanum Complex", *Tetrahedron Letters*, 34(5):851–854 (1993).

Kobayashi, S., et al., "Catalytifc Asymmetric Aldol Reaction of the Silyl Enol Ether of Acetic Acid Thioester with Aldehydes Using Chiral Tin(II) Lewis Acid", *Tetrahedron: Asymmetry*, 2(7):635–638 (1991).

Parmee, E. R., et al., "New Catalysts for the Asymmetric Aldol Reaction: Chiral Boranes Prepared from α,α–Disubstituted Glycine Arenesulfonamides", *J. Am. Chem. Soc.*, 113:9365–9366 (1991).

Furuta, K., et al., "Chiral (Acyloxy) borane Catalyzed Asymmetric Aldol Type Reaction of Ketene Silyl Acetals with Aldehydes", *SYNLETT*, :439 (1991).

Kiyooka, S., et al., "The Catalytic Asymmetric Aldol Reaction of Silyl Ketene Acetals with Aldehydes in the Presence of a Chiral Borane Complex. Nitroethane as a Highly Effective Solvent for Catalytic Conditions[1]", *Tetrahedron Letters*, 33(34): 4927–4930 (1992).

Parmee, E. R., et al., "The Catalytic Asymmetric Aldol Reaction of Aldehydes with Unsubstituted and Monosubstituted Silyl Ketene Acetals: Formation of Anti–β–Hydroxy–α–Methyl Esters", *Tetrahedron Letters*, 33(13):1729–1732 (1992).

Hayashi, M., et al., "Enantioselective Trimethylsilycyanation of Some Aldehydes Catalyzed by Chiral Schiff Base–Titanium Alkoxide Complexes", *J. Org. Chem.*, 58:1515–1522 (1993).

Nitta, H., et al., "Peptide–Titanium Complex as Catalyst for Asymmetric Addition of Hydrogen Cyanide to Aldehyde", *J. Am. Chem. Soc.*, 114:7969–7975 (1992).

Mikami, K., et al., "Asymmetric Catalytic Aldol–type Reaction with Ketene Silyl Acetals: Possible Intervention of the Silatropic Ene Pathway", *J. Am. Chem., Soc.*, 116:4077–4078 (1993).

Kobayashi, S., et al., "Catalytic Asymmetric Aldol–type Reaction Using a Chiral Tin(II) Lewis Acid #", *Tetrahedron*, 49(9):1761–1772 (1993).

*Primary Examiner*—Porfirio Nazario-Gonzalez
*Attorney, Agent, or Firm*—Flehr, Hohbach, Test, Albritton & Herbert; Richard F. Trecartin; Robin M. Silva

[57] ABSTRACT

The invention relates to catalysts for the synthesis of β-hydroxy carbonyl compounds, and in particular to enantioselective catalysts.

27 Claims, 10 Drawing Sheets

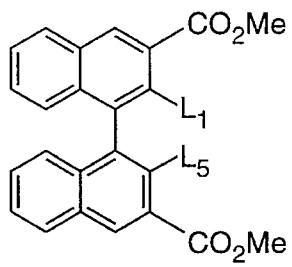
FIG._1A
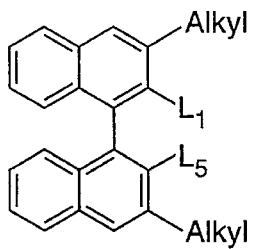
FIG._1B
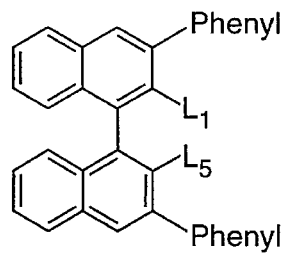
FIG._1C
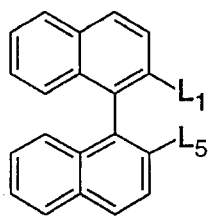
FIG._1D
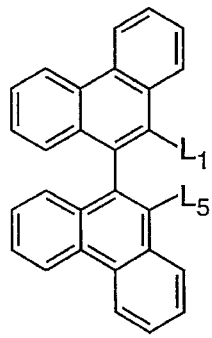
FIG._1E
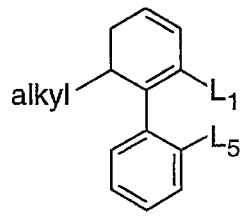
FIG._1F
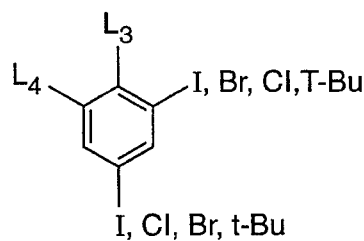
$L_3$ = OH, $L_4$ = COOH
FIG._3A
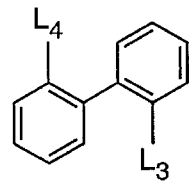
$L_3$ = OH, $L_4$ = COOH
FIG._3B
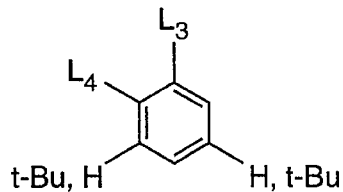
$L_3$ = OH, $L_4$ = OH
FIG._3C
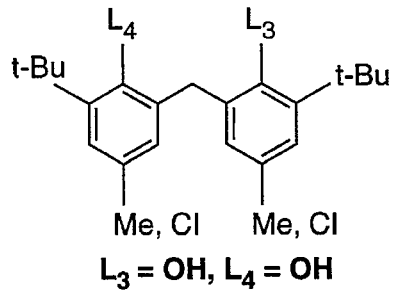
$L_3$ = OH, $L_4$ = OH
FIG._3D

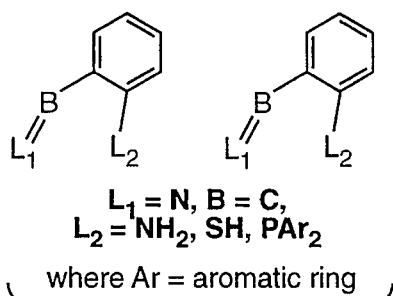
$L_1$ = N, B = C,
$L_2$ = $NH_2$, SH, $PAr_2$
where Ar = aromatic ring
FIG._2A
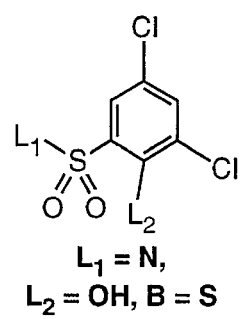
$L_1$ = N,
$L_2$ = OH, B = S
FIG._2B
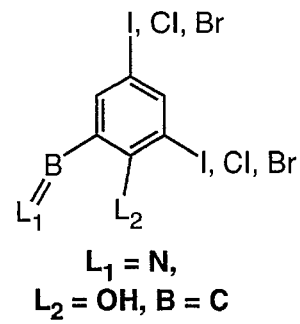
$L_1$ = N,
$L_2$ = OH, B = C
FIG._2D
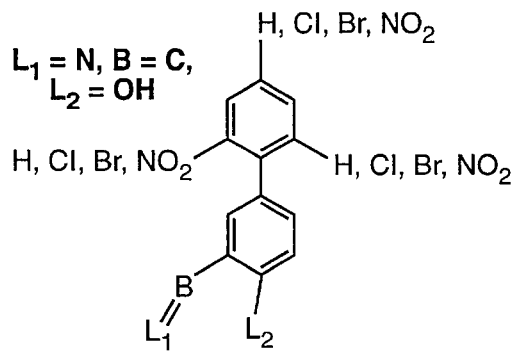
$L_1$ = N, B = C,
$L_2$ = OH
FIG._2C
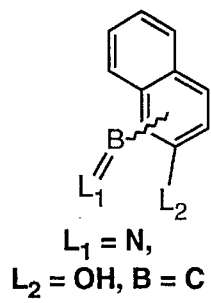
$L_1$ = N,
$L_2$ = OH, B = C
FIG._2E
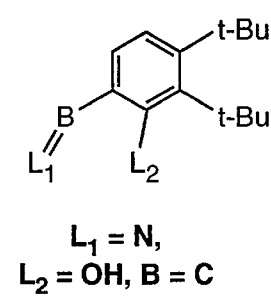
$L_1$ = N,
$L_2$ = OH, B = C
FIG._2F
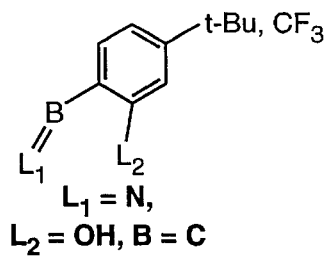
$L_1$ = N,
$L_2$ = OH, B = C
FIG._2G
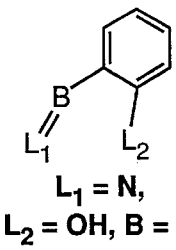
$L_1$ = N,
$L_2$ = OH, B = C
FIG._2H
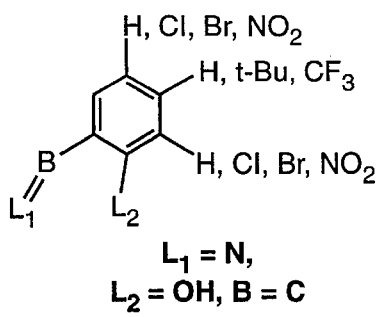
$L_1$ = N,
$L_2$ = OH, B = C
FIG._2I
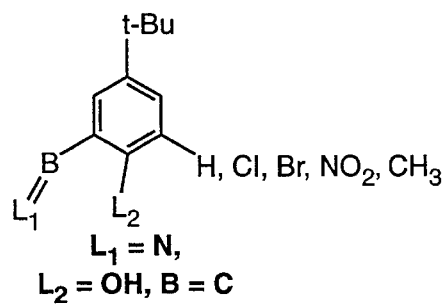
$L_1$ = N,
$L_2$ = OH, B = C
FIG._2J
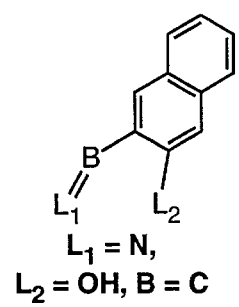
$L_1$ = N,
$L_2$ = OH, B = C
FIG._2K
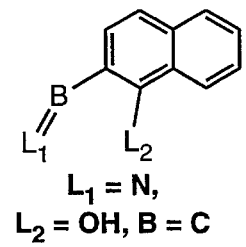
$L_1$ = N,
$L_2$ = OH, B = C
FIG._2L

Y = H, X = Z = halide
X = Z = H, Y = CF$_3$ or t-Bu
X = Z = halide, Y = CF$_3$ or t-Bu
X = t-Bu or Ph, Z = H or halide,
Y = CF$_3$ or t-Bu
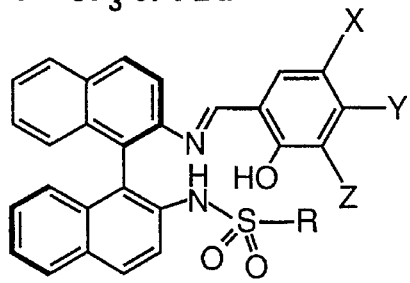
FIG._4A
Y = H, X = Z = halide
X = Z = H, Y = CF$_3$ or t-Bu
X = Z = halide, Y = CF$_3$ or t-Bu
X = t-Bu or Ph, Z = H or halide,
Y = CF$_3$ or t-Bu
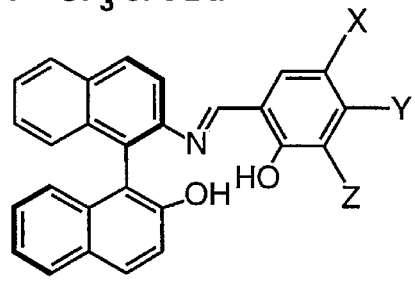
FIG._4B
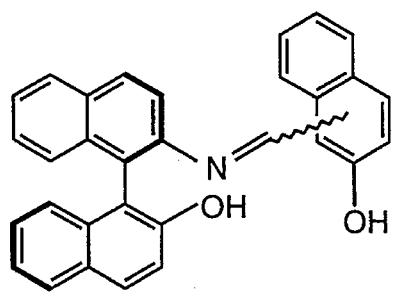
FIG._4C
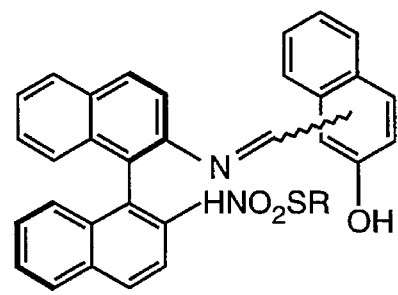
FIG._4D
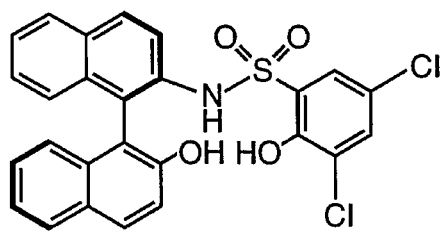
FIG._4E
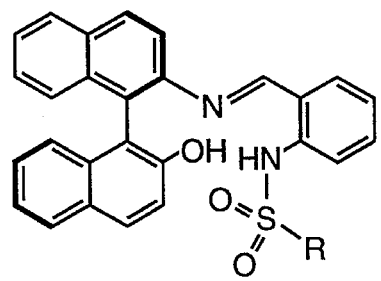
FIG._4F

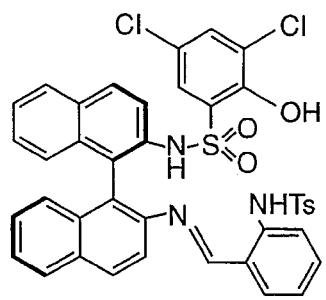
FIG._5A
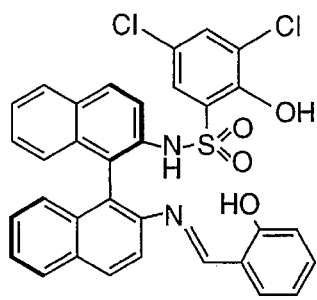
FIG._5B
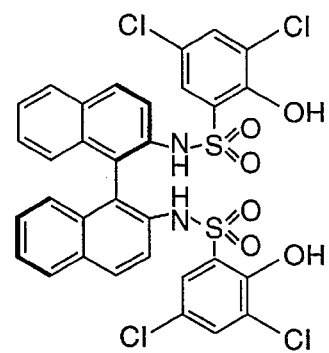
FIG._5C
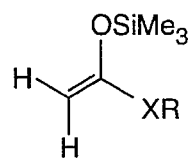
64 X = O
65 X = S
Acetate Enolate
R = Me, Et, Pr, $^t$Bu, Ph, 2,6–Me$_2$Ph
FIG._6A
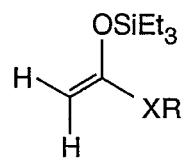
66 X = O
67 X = S
Acetate Enolate
R = Me, Et, Pr, $^t$Bu, Ph, 2,6–Me$_2$Ph
FIG._6B
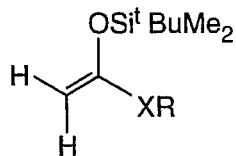
68 X = O
69 X = S
Acetate Enolate
R = Me, Et, Pr, $^t$Bu, Ph, 2,6–Me$_2$Ph
FIG._6C
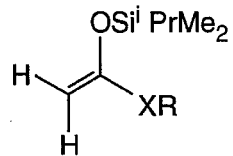
70 X = O
71 X = S
Acetate Enolate
R = Me, Et, Pr, $^t$Bu, Ph, 2,6–Me$_2$Ph
FIG._6D

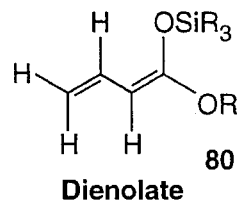

80
Dienolate
R = Me, Et, Pr, $^t$Bu, Ph, 2,6–Me$_2$Ph

*FIG._6E*

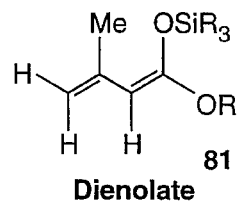

81
Dienolate
R = Me, Et, Pr, $^t$Bu, Ph, 2,6–Me$_2$Ph

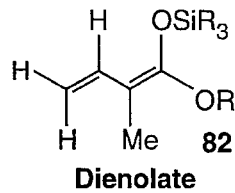

82
Dienolate
R = Me, Et, Pr, $^t$Bu, Ph, 2,6–Me$_2$Ph

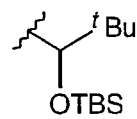

83
Ketone Enolate
R = Me, Et, Pr, $^t$Bu, Ph

*FIG._6H*

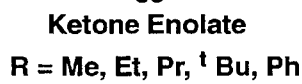

Ketone Enolate
R = Me, Et, Pr, $^t$Bu, Ph

*FIG._6I*

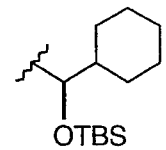

Ketone Enolate
R = Me, Et, Pr, $^t$Bu, Ph

*FIG._6J*

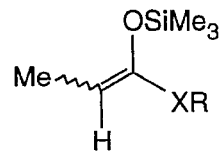

72 X = O, Z   74 X = O, E
73 X = S, Z   75 X = S, E
Propionate Enolate
R = Me, Et, Pr, $^t$Bu, Ph, 2,6–Me$_2$Ph

*FIG._6K*

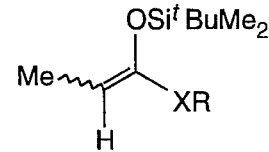

76 X = O, Z   78 X = O, E
77 X = S, Z   79 X = S, E
Propionate Enolate
R = Me, Et, Pr, $^t$Bu, Ph, 2,6–Me$_2$Ph

*FIG._6L*

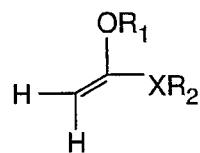

Propionate Enolate
X = O, S
R$_1$ = TMS, SiEt$_3$, Si-t-BuMe$_2$, SiPrMe$_2$
R$_2$ = Me, Et, Pr, t-Bu, P, 2,6–Me$_2$Ph

*FIG._6M*

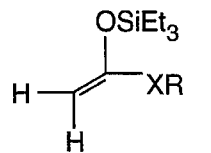

Propionate Enolate
X = O, S
R = alkyl

*FIG._6N*

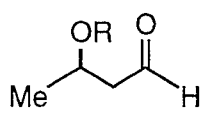
53a R = TBS
53b R = Bn
*FIG._7A*
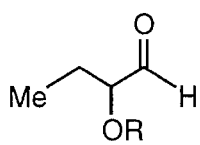
54a R = TBS
54b R = Bn
*FIG._7B*
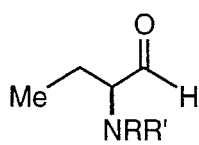
55a R = Cbz R' = H
55b R = R' = Bn
*FIG._7C*
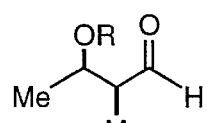
56a R = TBS
56b R = Bn
*FIG._7D*
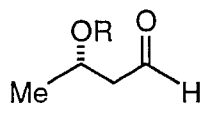
53c R = TBS
53d R = Bn
*FIG._7E*
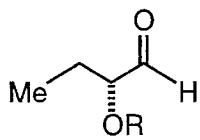
54c R = TBS
54d R = Bn
*FIG._7F*
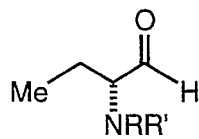
55c R = Cbz R' = H
55d R = R' = Bn
*FIG._7G*
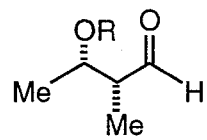
56c R = TBS
56d R = Bn
*FIG._7H*
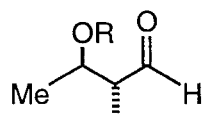
57a R = TBS
57b R = Bn
*FIG._7I*
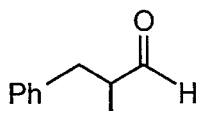
58a R = TBS
58b R = Bn
*FIG._7J*
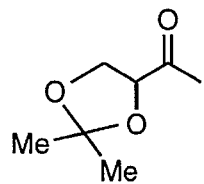
59a
*FIG._7K*
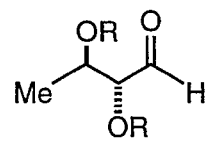
60a R = TBS
60b R = Bn
*FIG._7L*
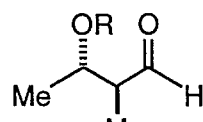
57c R = TBS
57d R = Bn
*FIG._7M*
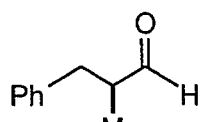
58c R = TBS
58d R = Bn
*FIG._7N*
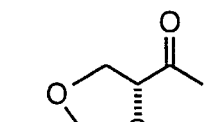
59b
*FIG._7O*
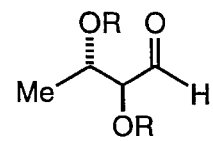
60c R = TBS
60d R = Bn
*FIG._7P*
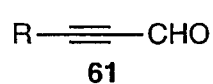
61
*FIG._7Q*
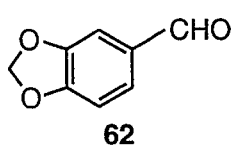
62
*FIG._7R*
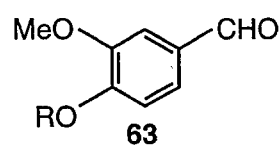
63
*FIG._7S*

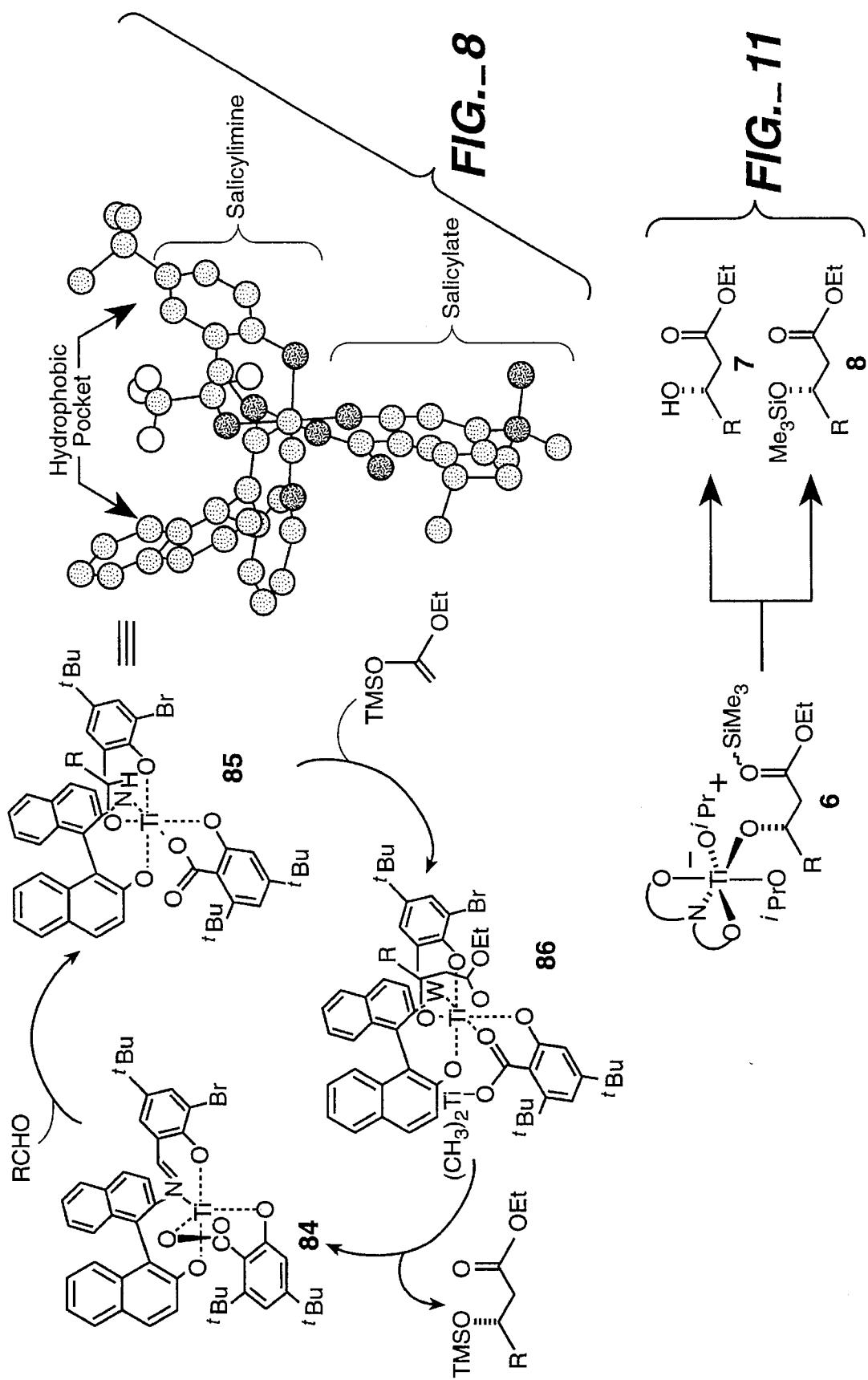

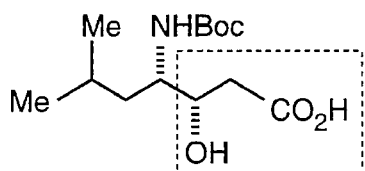
BOC-SATIN
(UPJOHN)
FIG._9A
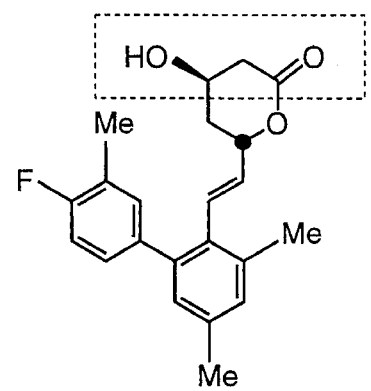
HMG CoA INHIBITOR
(MERCK & CO)
FIG._9B
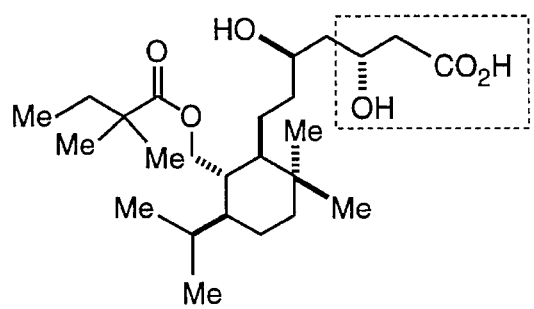
HMG CoA INHIBITOR
(BRISTOL MYERS SQUIBB)
FIG._9C
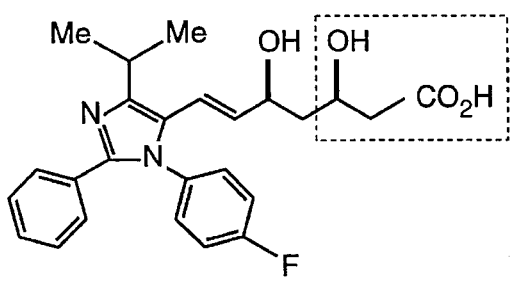
HMG CoA INHIBITOR SDZ 64-406
(SANDOZ)
FIG._9D
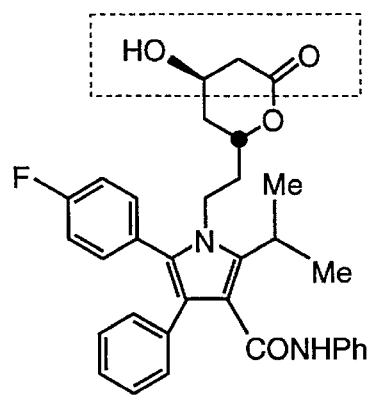
HMG CoA INHIBITOR
(PARKE DAVIS)
FIG._9E

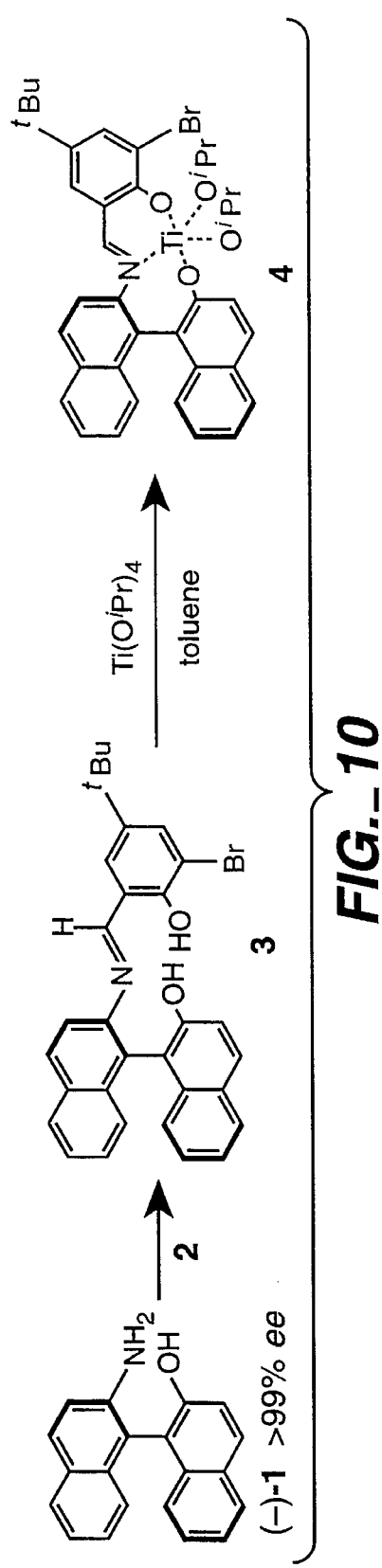
FIG._10
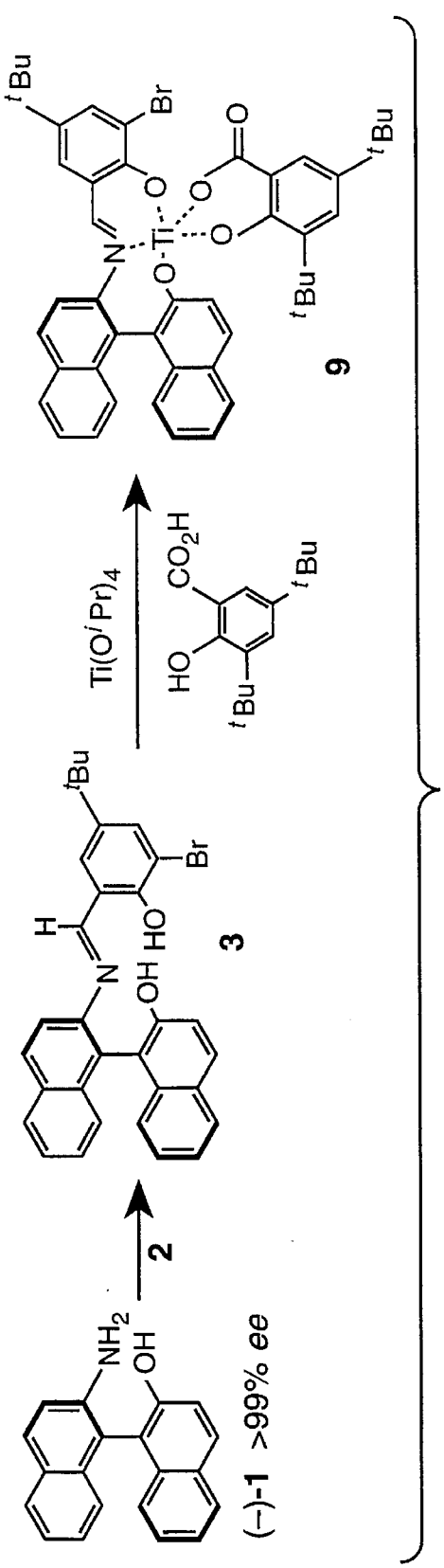
FIG._12

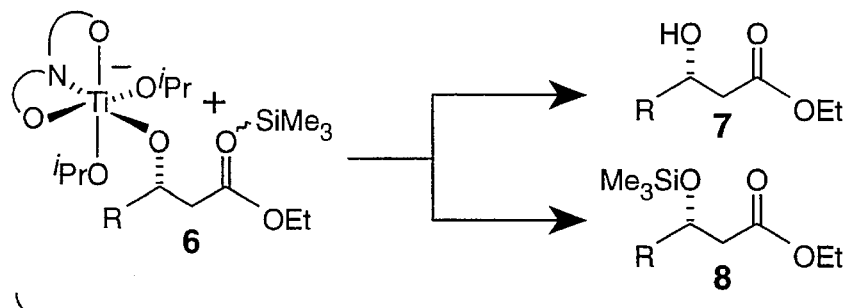

FIG._13

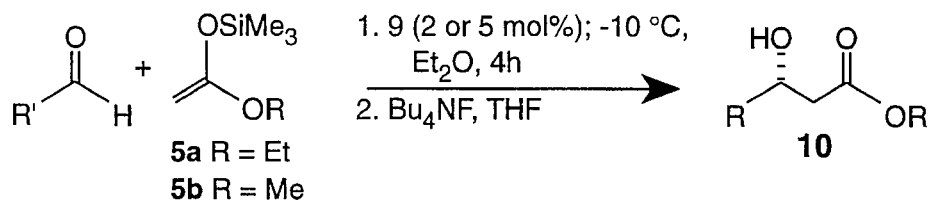

5a R = Et
5b R = Me

Absolute configuration of 10 was determined by reduction to the known 1,3-diols.

FIG._14A

Catalytic Asymmetric Aldol Additions of Alkyl Acetate Ketene Acetal[a,b]

| Entry | Aldehyde | ee: R = Et[c] | ee: R = Me[d] |
|---|---|---|---|
| 1 | Me-CH=CH-CHO | 92% | 98% |
| 2 | Me-CH2-CH2-CHO | 88% | 95% |
| 3 | Ph-CH=CH-CHO | 93% | 98% |
| 4 | Ph-CH2-CH2-CHO | 89% | 94% |
| 5 | $C_6H_{11}CHO$ | 94% | 95% |
| 6 | PhCHO | 93% | 96% |

[a]Yields for two steps (addition and desilylation) range from 72%-98%; [b]For each entry, the ee was determined by preparation of the derived (S)-MTPA ester and analysis by $^1$H NMR spectroscopy. [c]5 mol% catalyst used; [d]2 mol% catalyst used.

FIG._14B

CATALYSTS FOR PRODUCTION OF β-HYDROXY CARBONYL COMPOUNDS

CROSS REFERENCE TO RELATED APPLICATION

This is a continuation-in-part application of U.S. Ser. No. 08/310,241, filed Sep. 21, 1994, now abandoned.

FIELD OF THE INVENTION

The invention relates to catalysts for the production of β-hydroxy carbonyl compounds, and in particular to enantioselective catalysts. Methods for the production of β-hydroxy carbonyl compounds are also disclosed.

BACKGROUND OF THE INVENTION

Asymmetric catalysis of the Mukaiyama aldol addition reaction has been reported with complexes derived from Al, B, Sn(II), and Ti(IV) (Mikami et al., J. Am. Chem. Soc. 116:4077 (1994); Kobayashi et al., Tetrahedron 49:1761 (1993); Corey et al., Tetrahedron Lett. 33:6907 (1992); Parmee et al., Tetrahedron Lett. 33:6907 (1992); Kiyooka et al., Tetrahedron Lett. 33:4927 (1992); Furuta et al., J. Am. .Chem. Soc. 113:1041 (1991); Furuta et al., Synlett (1991) 439; Parmee et al., J. Am. Chem. Soc. 113:9365 (1991); Kiyooka et al., J. Org. Chem. 56:2276 (1991); Kobayashi et al. Tetrahedron: Asymm. 2:635 (1991); and Reetz et al. Chem. and Ind. (London) 1986, 824). The levels of asymmetric induction for the addition of propionate, isobutyrate, and acetate derived silyl thioketene acetals to aldehydes parallel those obtained with chiral auxiliary-based methodologies (Evans, Aldrich Chemica Acta 15:23 (1982); Heathcock, in The Aldol Addition Reaction, Morrison, Ed. Asymmetric Synthesis; Academic Press, San Diego, CA 1984, Vol. 3, Chapter 2). However, silyl ketene acetals derived from O-alkyl acetates uniformly provide aldolates possessing lower levels of asymmetric induction.

The design of ligands for catalysts for the Mukaiyama aldol addition have primarily included bidentate chelates derived from optically active diols (Mikami et al., supra, Reetz et al., supra), diamines (Kobayashi et al., 1993, supra; Kobayashi et al., 1991, supra), amino acids (Corey et al., supra, Parmee et al., 1992, supra; Kiyooka et al., 1992, supra; Parmee et al., 1991 supra; Kiyooda et al., 1991, supra) and tartrates (Furuta et al., 1991, supra; Furuta et al., 1991, supra). Enantioselective reaction processes utilizing chiral Ti(IV) complexes have proven to be some of the most powerful transformations available to the synthetic chemist (Hanson et al., J. Am. Chem. Soc., 109:5765 (1987); Duthaler et al. Chem. Rev. 92:807 (1992)). However, the propensity of Ti(IV) complexes to form multinuclear aggregates results in complex dynamic equilibria that can render mechanistic and structural analysis difficult.

Therefore, it is an object of the present invention to provide catalysts for the enantioselective synthesis of β-hydroxy carbonyl compounds.

SUMMARY OF THE INVENTION

In one aspect, the present invention provides compositions comprising compounds with structure 1:

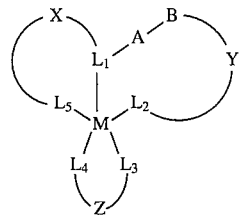

wherein:
M is selected from the group consisting of Fe, Ni, Cu, Sc, Y, La, Ti, Zr, Co and Hf;
$L_1$, $L_2$, $L_3$, $L_4$ and $L_5$ are each selected from the group consisting of O, N, S and P;
A is either a single or a double bond;
B is selected from the group consisting of C, N, S and P;
X is substituted biphenyl or substituted or unsubstituted: binaphthyl or bisphenanthrol;
Y is substituted phenyl, substituted naphthyl, or substituted biphenyl; and
Z is substituted or unsubstituted phenyl, biphenyl, or diphenyl-methane.

In another aspect, the invention provides compositions comprising compounds with structure 2:

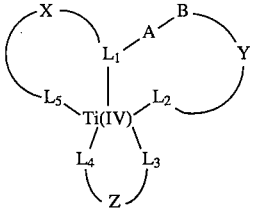

wherein:
$L_1$ is nitrogen;
$L_2$, $L_3$, $L_4$ and $L_5$ are each oxygen;
A is either a single or a double bond;
B is selected from the group consisting of C, N, S and P;
X is substituted biphenyl or substituted or unsubstituted: binaphthyl or bisphenanthrol;
Y is substituted phenyl, substituted naphthyl, or substituted biphenyl; and
Z=is substituted or unsubstituted phenyl, biphenyl, or diphenyl-methane.

In a further aspect, the invention provides compositions comprising compounds with structure 7:

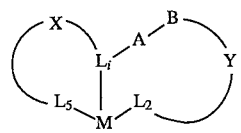

wherein:
M is selected from the group consisting of Fe, Ni, Cu, Sc, Y, La, Ti, Zr, Co and Hf;
$L_1$, $L_2$ and $L_5$=are each selected from the group consisting of O, N, S and P;
A is either a single or a double bond;
B is selected from the group consisting of C, N, S and P;
X is substituted biphenyl or substituted or unsubstituted: binaphthyl or bisphenanthrol; and Y=substituted phenyl, substituted naphthyl, or substituted biphenyl.

In a further aspect, the invention provides processes for making β-hydroxy carbonyl compounds. The method comprises contacting an aldehyde and an activated alkene, such as a substituted enolate, with a compound of the present invention.

BRIEF DESCRIPTION OF THE DRAWINGS

FIGS. 1A, 1B, 1C, 1D, 1E and 1F depict preferred X moieties.

FIGS. 2A, 2B, 2C, 2D, 2E, 2F, 2G, 2H, 2I, 2J, 2K, and 2M depict preferred Y moieties. In FIGS. 2A and 2B, $L_1$=N, B=C,$L_2$=$NH_2$, SH, $PAr_2$, where Ar=an aromatic ring. In FIG. 2C, $L_1$=N, $L_2$=OH, and B=S. In FIG. 2D, $L_1$=N, B=C, and $L_2$=OH. In FIGS. 2E through 2M, $L_1$=N, $L_2$=OH, and B=C.

FIGS. 3A, 3B, 3C and 3D depict preferred Z moieties. In FIGS. 3A and 3B, $L_3$=OH, $L_4$=COOH. In FIGS. 3C and 3D, $L_3$=OH, and $L_4$=OH.

FIGS. 4A, 4B, 4C, 4D, 4E and 4F depict tridentate ligands. In FIGS. 4A and 4B, when Y=H, X=Z=halide; when X=Z=H, Y=$CF_3$ or t-Bu; when X=Z=halide, Y=$CF_3$ or t-Bu; when X=t-Bu or Ph, Z=H or halide and Y=$CF_3$ or t-Bu.

FIGS. 6A, 6B, 6C, 6D, 6E, 6F, 6G, 6H, 6I, 6J, 6K, 6L, 6M, and 6N depict preferred substituted enolates. FIGS. 6A, 6B, 6C and 6D are acetate enolates, and R=Me, Et, Pt, t-Bu, Ph, 2,6-$Me_2$Ph. In FIG. 6A, compound 64 comprises X=O, and compound 65 is X=S. In FIG. 6B, compound 66 comprises X=O, and compounds 67 is X=S. In FIG. 6C, compound 68 comprises X=O, and compound 69 is X=S. In FIG. 6D, compound 70 comprises X=O, compound 71 is X=S. FIGS. 6E, 6F and 6G are dienolates, where R=Me, Et, Pr, t-Bu, Ph, 2,6-$Me_2$Ph. FIGS. 6H, 6I and 6J are ketone enolates, where R=Me, Et, Pr, t-Bu, Ph. FIGS. 6K, 6L, 6M and 6N are propionate enolates, where R=Me, Et, Pr, t-Bu, Ph, 2,6-Me2Ph. Compound 72 comprises X=O, Z; compound 73 comprises X=S, Z; compound 74 comprises X=O, E; compound 75 comprises X=S, E; compound 76 comprises X=O, Z; compound 77 comprises X=S, Z; compound 78 comprises O, E; and compound 79 comprises X=S, E. In FIG. 6M, X=O, S; $R_2$=Me, Et, Pr,t-Bu, 2,6-$Me_2$Ph; and $R_1$=TMS, $SiEt_3$, Si-t-$BuMe_2$, $SiPrMe_2$. In FIG. 6N, R=alkyl and X=O, S.

FIGS. 7A, 7B, 7C, 7D, 7E, 7F, 7G, 7H, 7I, 7J, 7K, 7L, 7M, 7N, 7O, 7P, 7Q, 7R and 7S depict preferred reactant aldehydes. In FIG. 7A, compound 53a comprises R=TBS, and compound 53b comprises R=Bn. In FIG. 7B, compound 54a comprises R=TBS, and compound 54b comprises R=Bn. In FIG. 7C, compound 55a comprises R=Cbz and R'=H, and compound 55b is R=R'=Bn. In FIG. 7D, compound 56a comprises R=TBS, and compound 56b comprises R=Bn. In FIG. 7E, compound 53c comprises R=TBS and compound 53d comprises R=Bn. In FIG. 7F, compound 54c comprises R=TBS and compound 54d comprises R=Bn. In FIG. 7G, compound 55c comprises R=Cbz and R'=H, and compound 55d comprises R=R'=Bn. In FIG. 7H, compound 56c comprises R=TBS and compound 56d comprises R=Bn. In FIG. 7I, compound 57a comprises R=TBS and compound 57b comprises R=Bn. In FIG. 7J, compound 58a comprises R=TBS and compound 58b comprises R=Bn. In FIG. 7K, compound 57c comprises R=TBS and compound 57d comprises R=Bn. In FIG. 7L, compound 58c comprises R=TBS and compound 58d comprises R=Bn. FIG. 7M is compound 59a. In FIG. 7N, compound 60a comprises R=TBS and compound 60b comprises R=Bn. In FIG. 7R, compound 60c comprises R=TBS and compound 60d comprises R=Bn. FIG. 7O is compound 62. FIG. 7P is compound 63. FIG. 7Q is compound 59a. FIG. 7S is compound 61.

FIG. 8 depicts a putative reaction mechanism for the catalysts of the present invention.

FIGS. 9A, 9B, 9C, 9D and 9E depict antihypertensive compounds; HMG-CoA refers to 3-hydroxyl-3-methyl-glutaryl-ScoA. FIG. 9A is Boc-Satin (Upjohn). FIG. 9B is HMG CoA inhibitor (Merck & Co.). FIG. 9C is HMG CoA inhibitor (Bristol Myers Squibb). FIG. 9D is HMG CoA inhibitor SDZ 64-406 (Sandoz). FIG. 9E is HMG CoA inhibitor (Parke Davis).

FIG. 10 depicts Scheme I, the synthesis of a tridentate enantioselective catalyst.

FIG. 11 depicts Scheme II, the reaction of a tridentate catalyst.

FIG. 12 depicts Scheme III, the synthesis of a pentadentate enantioselective catalyst.

FIG. 13 depicts Scheme IV, the reaction of a pentadentate catalyst.

FIG. 14A depicts the aldol addition reaction. FIG. 14B depicts the results in tabular form of some of the aldol addition reactions using a pentadentate catalyst. a) Absolute configuration was determined by reduction to the known 1,3-diols; b) Yields for two steps (addition and desilylation) range from 72–98%; c) for each entry, the ee was determined by preparation of the derived (S)-MTPA ester and analysis by $^1$H NMR spectroscopy; d) 5 mol % catalyst used; e) 2 mol % catalyst used.

DETAILED DESCRIPTION OF THE INVENTION

At the broadest level, the present invention provides metal containing catalysts for the synthesis of β-hydroxy carbonyl compounds and β-hydroxy alkenes. Preferably, these catalysts contain at least one chiral center which confers enantioselectivity on the catalyst.

The present invention provides compounds having the structure shown in Structure I:

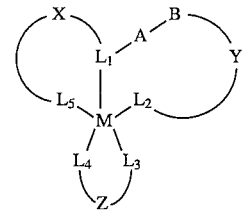

wherein:

M is selected from the group consisting of Fe, Hi, Cu, Sc, Y, La, Ti, Zr, Co and Hf;

$L_1$, $L_2$, $L_3$, $L_4$ and and $L_5$ are each selected from the group consisting of O, N, S and P;

A is either a single or a double bond;

B is selected from the group consisting of C, N, S and P;

X is substituted biphenyl or substituted or unsubstituted: binaphthyl or bisphenanthrol;

Y is substituted phenyl, substituted naphthyl, or substituted biphenyl; and

Z is substituted or unsubstituted phenyl, biphenyl, or diphenyl-methane.

In this embodiment, the compound consists of a metal atom with at least five ligand coordination groups or moieties, $L_1$, $L_2$, $L_3$, $L_4$ and $L_5$, which are part of a multidentate ligand. The ligand coordination groups comprise at least a coordination atom. Suitable coordination atoms are oxygen, nitrogen, sulfur or phosphorus atoms. In one embodiment, the ligand coordination group comprises only a coordination atom. In alternative embodiments, the ligand coordination group comprises a substituent group, as outlined below, which contains a suitable coordination atom. Thus, for example, a carboxy group may be the ligand coordination group, and the hydroxy oxygen of the carboxyl group is the coordination atom. This embodiment is exemplified by the $L_3$ ligand coordination group in Structure 3:

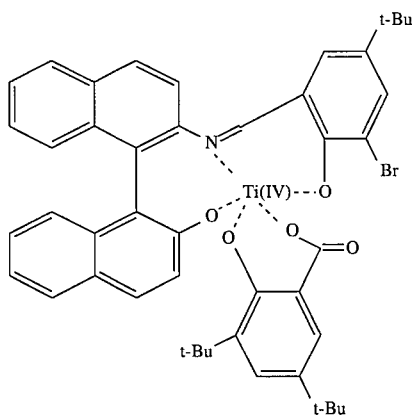

Preferred oxidation states for the metals are as follows: titanium is +4, scandium is +3, zirconium is +4, yttrium is +3, lanthanum is +3, hafnium is +4, copper is either +2 or +1, nickel is +2, cobalt is either +2 or +3, and iron is either +2 or +3.

As is understood by those in the art, the selection of the coordination atoms will depend in part on the metal, M, used in the compound. For example, preferred coordination atoms for titanium (Ti) include oxygen, although nitrogen may also be the coordination atom. Thus, when Ti is the metal, four oxygens and a nitrogen are preferred. Scandium (Sc), zirconium (Zr), yttrium (Y), lanthanum (La) and hafnium (Hf) also prefer oxygen as a coordination atom.

In an alternative embodiment, when copper (Cu), nickel (Ni), cobalt (Co) or iron (Fe) is the metal atom, the coordination atoms of the ligands are preferably sulfur (S), phosphorus (P) or nitrogen (N).

In a preferred embodiment, the A bond is a double bond. In this embodiment, the coordination atom of $L_1$ may be nitrogen, sulfur or phosphorus. If the coordination atom of $L_1$ is sulfur or phosphorus, there may be one or more hydrogen atoms attached to the coordination atom, to form the $L_1$ ligand coordination group.

In an alternative embodiment, the A bond is a single bond. In this embodiment, the coordination atom of $L_1$ may be nitrogen, oxygen, sulfur or phosphorus. If the coordination atom of $L_1$ is nitrogen, sulfur or phosphorus, $L_1$ may have one or more hydrogen atoms attached, or in the case of phosphorus, an alkyl group may be attached.

The "X" group or moiety may be substituted or unsubstituted binaphthyl or-bisphenanthrol, of substituted biphenyl, as described below.

By "binaphthyl" herein is meant a binaphthyl moiety, as shown below in Structure 4 with $L_1$ and $L_5$ as described herein:

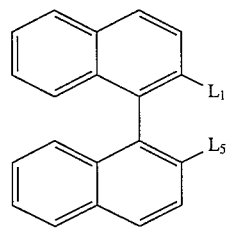

It is to be understood that the binaphthyl moiety, with the attached $L_1$ and $L_5$ moieties, is a chiral moiety. While not containing a stereogenic center per se, the hindered rotation around the single bond between the two naphthyl groups confers chirality. As a result, the binaphthyl moiety may be produced in either the (+) or (−) conformation.

By "biphenyl" herein is meant a biphenyl moiety, as shown below in Structure 5 with the $L_1$ and $L_5$ coordination atoms as described herein:

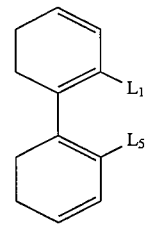

The biphenyl moiety is preferably substituted, as defined below, in at least one position ortho to the single bond, in addition to the ligand coordination groups. The substitution group is chosen so that it is large enough to restrict the rotation around the single bond and thus confer chirality to the biphenyl moiety, similar to the binaphthyl as outlined above. Thus, as above, biphenyl moieties can be made in either the (+) or (−) conformation.

In addition to the ligand coordination groups which are attached in appropriate ortho positions on each ring of the biphenyl, there is at least an additional substituent group in at least one of the two remaining ortho positions. In an alternative embodiment, there is an additional substituent group in the remaining ortho position. In addition to the ortho position substitution, the biphenyl may be additionally substituted, as outlined below.

By "bisphenanthrol" herein is meant a bisphenanthrol moiety, as shown below in Structure 6 with $L_1$ and $L_5$ as described herein:

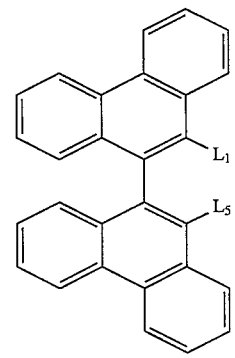

Similar to the binaphthyl moiety, the bisphenanthrol moiety is a chiral moiety, since rotation around the single bond is restricted due to the $L_1$ and $L_5$ ligand coordination moieties, and the fused aromatic group of the phenanthrol. Accordingly, the bisphenanthrol moiety may be made in either the (+) or (−) orientations.

As is described below, it is the chirality of the X moiety which renders the catalysts of the present invention enantioselective. The chiral characteristic of the X moiety is preferably the only chirality of the catalysts of the invention, although other embodiments utilize Y and/or Z moieties which have chirality as well. Thus, as is further detailed below, the selection of the (+) form of the X moiety will give one enantiomer as a product in enantiomeric excess; the (−) form of the X moiety will give the opposite enantiomer as a product in enantiomeric excess.

Particularly preferred X moieties are shown in FIG. 1, with the $L_1$ and $L_5$ coordination atoms labelled as such.

The "Y" group or moiety is substituted phenyl, substituted naphthyl, or substituted biphenyl. In a preferred embodiment, the biphenyl group does not have any chiral character, although other embodiments utilize substituted biphenyl groups with chiral attributes. As described below, the substitution groups are in addition to the B atom and the $L_2$ ligand coordination group which are attached to the Y moiety as shown.

Particularly preferred Y groups are shown in FIG. 2, with $L_1$ and the B atom, and the A bond, i.e. either a double or single bond, between $L_1$ and B as shown.

The "Z" moiety or group, is substituted or unsubstituted phenyl, biphenyl, or diphenyl-methane. That is, $L_3$ and $L_4$ may be the only substituent groups, or there may be additional substituent groups on the Z moiety. The biphenyl moiety of the Z group does not have the same requirement as the X moiety for substitution in the ortho position. Rather, the Z moiety, if substituted, may be substituted at any position. As for the Y moiety, in a preferred embodiment the substituted biphenyl and substituted diphenyl-methane do not have chiral characteristics. Other embodiments utilize a Z moiety with chiral attributes.

Particularly preferred Z groups are shown in FIG. 3, with the $L_3$ and $L_4$ ligand coordination groups labelled as such.

By "substituted" herein is meant that an aromatic ring of ligands X, Y or Z has at least one substituent group replacing a hydrogen group. These substituent groups are in addition to the ligand coordination groups; thus, for example, if the X moiety is binaphthyl, the $L_1$ and $L_5$ ligand coordination groups are substituent groups of the binaphthyl. However, as generally used herein, substituent groups are additional to the L ligand coordination groups, and thus are substituent groups at other positions. Thus, an unsubstituted X, Y or Z moiety will still have the ligand coordination groups.

Suitable substituent groups include, but are not limited to, alkyl groups, halogens, nitro groups, sulfonate groups, carboxy groups, aldehydes, ketones, alcohols, amines, ammonium, phosphonates, sulfones or sulfoxides.

In some embodiments, the X, Y and Z moieties are substituted in at least one position in addition to the ligand coordination group. In alternative embodiments, the moieties are substituted in more than one position, and may be substituted at every position. Similarly, in some embodiments, the binaphthyl and bisphenanthrol moieties are symmetrically substituted. By "symmetrically substituted" herein is meant that the binaphthyl or bisphenanthrol moiety has at least $C_2$ symmetry when the bonds of the molecule are maximally constrained in a single plane. In some instances, there will be $C_{2v}$ symmetry. These binaphthyl or bisphenanthrol moieties are generated by joining two identically substituted naphthyl or phenanthrol moieties. In other embodiments, the substitution is not symmetric; that is, each naphthyl or phenanthrol is substituted differently. For example, one naphthyl or phenanthrol may be substituted in one or more positions, and the other is not substituted at all.

By "alkyl" or "alkyl group" or grammatical equivalents herein is meant a straight or branched chain alkyl group, with straight chain alkyl groups being preferred. If branched, it may be branched at one or more positions, and unless specified, at any position. Also included within the definition of an alkyl group are cycloalkyl groups such as C5 and C6 rings, aromatic rings such as phenyl, heterocyclic aromatic rings such as pyridine, furan, thiophene, pyrrole, indole and purine, and heterocyclic rings with nitrogen, oxygen, sulfur or phosphorus.

In one embodiment, the alkyl groups may also be substituted with halogens, nitro groups, alcohols, carboxy groups, amines, or sulfonates. For example, substituent groups such as $CF_3$, silyl derivatives such as trialkyl silyl, including trimethyl silyl, triethyl silyl, tri-isopropyl silyl and tri-amyl silyl, are preferred.

The alkyl group may range from about 1 to 20 carbon atoms (C1–C20), with a preferred embodiment utilizing from about 1 to about 10 carbon atoms (C1–C10), with about C1 through about C6 being preferred. However, in some embodiments, the alkyl group may be larger, particularly if it is a straight chain alkyl.

Particularly preferred alkyl groups include t-butyl, iso-propyl, cyclohexyl, adamatyl, iso-amyl, p-amyl, ioctyl and t-octyl.

By "halogen" herein is meant halogens such as bromine, fluorine, and chlorine.

By "nitro group" herein is meant a —$NO_2$ group.

By "sulfonate group" herein is meant a —$SO_3H$, —$SO_2(alkyl)_2$, or —$SO(alkyl)_3$ group. By "sulfoxide group" herein is meant a RSOR group, with R being an alkyl as defined above. By "sulfone" herein is meant a $R_2SO_2$ group, with R being an alkyl group as defined above.

By "carboxy group" herein is meant a —COOH group.

By "aidehyde" or "formyl group" herein is meant a —CHO group. In a preferred embodiment, the aldehyde is a alkyl aidehyde, with the alkyl group being defined as above.

By "ketone" herein is meant a —COR group, with R being an alkyl group as defined above.

By "alcohol" herein is meant an —OH group or an alkyl alcohol, wherein the alkyl group is defined as above. In a preferred embodiment, the substituent group is an —OH group. In alternative embodiments, the alcohol is an alkyl alcohol. The alkyl alcohol may be primary, secondary or tertiary, depending on the alkyl group.

By "amine group" or "amine" herein is meant a —$NH_2$, —NHR, or —$NR_2$ group, with R being an alkyl group as defined above. Thus, the amine may be a primary, secondary, or tertiary amine. In a preferred embodiment, the amine is a —$NH_2$ group. An "ammonium group" is a —$NH_4+$ group.

In a further embodiment, the X, Y and Z moieties may be substituted with a linker group, such that the compound may be linked to a solid support, using techniques well known in the art. For example, the linker may be a carboxyl, sulfonate or phosphonate moiety. By "phosphonate" herein is meant a —$PO(OH)_2$ or —$PO(OR)_2$ group, with R being an alkyl as defined above. In a preferred embodiment, there is a single linker substituent on the compound.

In an additional embodiment, the compounds of the invention have the structure shown in Structure 2:

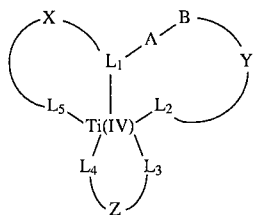

In this embodiment, $L_1$ is nitrogen;

$L_2$, $L_3$, $L_4$ and $L_5$ are each oxygen;

A is either a single or a double bond;

B is selected from the group consisting of C, N, S and P;

X is substituted or unsubstituted: binaphthyl, biphenyl, or bisphenanthrol;

Y is substituted phenyl, substituted naphthyl, or substituted biphenyl; and

Z is substituted or unsubstituted phenyl, biphenyl, diphenyl-methane.

The compounds of the present invention are generally synthesized as follows. The X moiety, with attached $L_1$ and $L_5$ ligand coordination groups, is synthesized using techniques well known in the art. The Y moiety, with an attached $L_2$ ligand coordination group, is also synthesized using known techniques, and the X and Y moieties are added together to form a tridentate ligand structure. The tridentate ligand structure is purified if necessary. Then the Z moiety is added to the tridentate ligand structure in the presence of the metal to form the compounds of the invention. In alternative embodiments, the Z moiety and the metal are added sequentially in any order. Further embodiments allow the addition of the X, Y, Z and metal atoms in any order.

In the case where the $L_1$ coordination atom is nitrogen, the Y moiety is frequently synthesized as an benzaldehyde derivative, which then reacts with a primary amine to form an imine bond.

Thus, it is possible to make compounds combining any X, Y and Z moieties. As noted above, the X moiety may be substituted biphenyl, or substituted or unsubstituted binaphthyl or bisphenanthrol, as described above. The Y moiety may be substituted phenyl, substituted naphthyl, or substituted biphenyl. The Z moiety, is phenyl, biphenyl, or diphenyl-methane, and may be either substituted or unsubstituted.

It is to be understood that this synthesis generally results in a compound with five coordination atoms for the metal atom. Generally, the compound is in two parts; a tridentate ligand, with three coordination atoms, and a bidentate ligand, with two coordination atoms, resulting in a pentadentate compound. In a preferred embodiment, the tridentate and bidentate ligands are not covalently attached, but instead are held together by binding to a common metal atom. In an alternative embodiment, the tridentate and bidentate ligands are covalently attached, for example, the X and Z moieties or the Y and Z moieties may be covalently attached, either directly or via a substitutent group.

In an alternative embodiment, the compounds of the present invention may be only tridentate ligands, as is exemplified in Example 1 and shown generally in the structure 7 below:

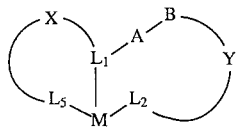

wherein

M is selected from the group consisting of Fe, Ni, Cu, Sc, Y, La, Ti, Zr and Hf;

$L_1$, $L_2$, and $L_5$ are each selected from the group consisting of O, N, S and P;

A is either a single or a double bond;

B is selected from the group consisting of C, N, S and P;

X is substituted biphenyl or substituted or unsubstituted: binaphthyl or bisphenanthrol; and Y is substituted phenyl, substituted naphthyl, or substituted biphenyl.

In this embodiment, the synthesis of the tridentate ligands proceeds as for the pentadentate ligands, except that only the X and Y moieties are used, and the metal is added either when X and Y are joined or afterwards.

The metal may have additional ligands, such as alcohols, acids, carboxylic acids, or sulfonates, attached in the $L_3$ and $L_4$ positions, but which are not attached to a Z moiety. Additional examples of tridentate ligands are shown in FIG. 4.

Alternatively, the compounds of the present invention may be tetradentate ligands. The tetradentate ligands have 4 ligand coordination groups, and are capable of catalyzing the synthesis of β-hydroxy carbonyls (aldol addition reactions) or β-hydroxy alkenes. Specific examples of tetradentate ligands are shown in FIG. 5.

Once synthesized, the compounds of the present invention are useful in a variety of applications. In a preferred embodiment, the compounds are useful as catalysts for the formation of β-hydroxy carbonyl compounds, sometimes referred to as "aldols". A β-hydroxy carbonyl compound is a compound with the structure 8 shown below; the R groups may be either identical or different.

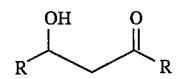

The hydroxy group in the B position may be generated in either orientation, depending on the chirality of catalyst used. As outlined above, preferably the catalyst is chiral as a result of the chirality of the X moiety. The chirality of the X moiety depends on the conformation of the binaphthyl, biphenyl or bisphenanthrol moiety. Thus, as an example, if the X moiety is made using the (−) enantiomer of binaphthyl, the resulting catalyst will generate β-hydroxy carbonyls where the hydroxy "goes into the page", using normal stereochemical depictions. Conversely, the (+) enantiomer of binaphthyl will generate a B-hydroxyl carbonyl where the hydroxy "comes out of the page".

Thus, in a preferred embodiment, the catalysts are generated using X moieties in enantiomeric excess. For example, the enantiomer used to generate the X moiety ranges from about 60% to about 99% enantiomeric excess (ee), with enantiomeric excesses of at least about 90%, at least about 95%, and 99% being preferred.

In alternative embodiments, the chirality of the catalyst is due to the chiral attributes of either the X, Y or Z moieties; i.e. at least one of X, Y or Z is chiral. In a preferred embodiment, only a single moiety is chiral due to the general expense of chiral molecules. In some embodiments, more than one of X, Y and Z is chiral. In these embodiments, the chirality of each moiety may either augment or suppress the enantioselectivity of the catalyst.

Generally, the compound catalyzes the production of β-hydroxy carbonyl compounds from a substituted enolate and an aldehyde. Depending on the reactants, the product may be β-hydroxy amides, β-hydroxy esters, β-hydroxy thioesters, β-hydroxy ketones, or β-hydroxy aldehydes.

The general reaction is shown below in Reaction 1, wherein an activated alkene, in this case an enolate, reacts with an aldehyde:

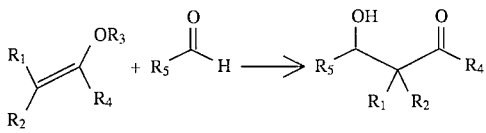

In this reaction, $R_1$, $R_2$ and $R_5$ may be an alkyl group, as defined above, or hydrogen, with hydrogen being preferred. $R_1$ and $R_2$ may also be alkoxy or amino groups, thus creating a "doubly activated" enolate or alkene.

$R_3$ may be an alkyl group, as described above, with methyl being preferred. In addition, nucleophilic enolates are particularly preferred, such as those with silyl derivatives as $R_3$; for example, trimethyl silyl, t-butyl dimethyl silyl, tri-isopropyl silyl, or triethyl silyl are preferred.

$R_4$ may be an ether, an amine, a hydrogen or an alkyl group. It is the $R_4$ group of the substituted enolate which defines the β-hydroxy product. Thus, if $R_4$ is an ether, the reaction product is a β-hydroxy ester; if $R_4$ is a thioether, the reaction product is a β-hydroxy thioester; if $R_4$ is an amine, the reaction product is a β-hydroxy amide. If $R_4$ is a hydrogen, the reaction product is a β-hydroxy aldehyde. If $R_4$ is an alkyl group, as defined above, the reaction product is a β-hydroxy ketone.

By "ether" herein is meant an —OR group, where R is an alkyl group.

Preferred substituted enolates, comprising silyl enol ethers, are shown in FIG. 6. Preferred enolates also include those in FIG. 6 wherein one or both of the vinyl hydrogens is substituted with $R_1$ and $R_2$ groups as defined above.

Additional embodiments utilize alkyl enol ethers as the substituted enolates. In such embodiments, the alkyl group is as defined above. Preferred enolates include those shown in FIG. 6 with the silyl group replaced with an alkyl group as defined above. Preferred alkyl groups include those with electron donating properties, such as benzyl and t-butyl, with electron withdrawing groups, such as nitro, being less desirable. A particularly preferred substituted enolate is 2-methoxypropene, i.e. methyl ether enolate, since it is an inexpensive commercial product. As with the silyl substituted enolates set forth in FIG. 6, one or both of the vinyl hydrogens in the alkyl ether enolates can be substituted with the $R_1$ and $R_2$ groups described above.

As will be appreciated by those skilled in the art, a wide variety of aldehyde reactants may be used in these reactions. Preferred aldehyde reactants are shown in FIG. 7.

In a preferred embodiment, the reactants are a substituted enolate and an aldehyde. In this embodiment, the product is a secondary alcohol. In an additional embodiment, the reactants are a substituted enolate and a ketone. In this embodiment, the product is a tertiary alcohol.

Without being bound by theory, a potential reaction mechanism is shown in FIG. 8, exemplified by the Structure 3 catalyst.

Similarly, those skilled in the art will appreciate that these reactions may be carried out in a variety of solvents. A variety of solvents may be used, including, but not limited to, $CH_2Cl_2$, $Et_2O$, $CH_3CN$, toluene, benzene, tetrahydrofuran, xylene, mesitylene, and cyclohexane. $Et_2O$ and toluene are particularly preferred.

When the substituted enolate is an alkyl enol ether, it may be preferred that the alkyl enol ether be used as the solvent to drive the reaction, due to the attenuated nucleophilicity of the alkyl enol ethers as compared to the silyl substituted enolates. Alternative embodiments do not require the alkyl enol ethers to be used as the solvent, but desirable reaction rates may require higher temperatures. In this embodiment, the unreacted alkyl enol ether may be removed upon completion of the reaction by vacuum or other known methods.

The use of the alkyl enol ether as the solvent may not be necessary when the alkyl group of the alkyl enol ether has electron donating properties, providing some level of nucleophilicity.

In a preferred embodiment, the catalyst compounds of the invention are enantioselective, that is, they generate an excess of one enantiomeric product over the other. Since the hydroxyl group in the β position may have either conformation, catalysts which produce an enantiomeric excess of one enantiomer over the other are particularly useful. This is particularly true since many biological products and drugs are active in one conformation but not the other. Enantiomeric excess is defined as the excess of the major product; thus if the products of the reaction are 89% enantiomer "X" and 11% enantiomer "Y", the enantiomeric excess is 89–11 or 78%. An enantioselective reaction produces an enantiomeric excess of greater than zero, although preferred enantiomeric excesses are greater than about 60%, with enantiomeric excesses greater than about 80%, 90% or 95% being particularly preferred.

In a preferred embodiment, the enantioselective reactions are carried out at temperatures less than 0° C., with preferred temperatures ranging from about −20° C. to 0° C. Temperatures above 0° C. may also be used, with preferred temperatures ranging from about 0° C. to about 30° C., with from about 0° C. to about room temperature being preferred.

The enantioselective catalysts of the present invention are particularly useful to generate antihypertensive compounds, such as those commercially produced and shown in FIG. 9.

In a further embodiment, the catalyst compounds of the invention are used to make S-hydroxy alkenes. This general reaction scheme 2 is outlined below:

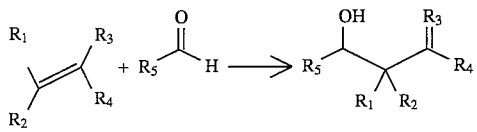

In this embodiment, the reactants are an aldehyde and an activated alkene such as a substituted ethylene. The $R_1$, $R_2$, $R_4$ and $R_5$ groups are defined as above. The activated alkenes are nucleophilic alkenes, with the $R_3$ group being responsible for the nucleophilic characteristic of the activated alkene. Thus the activated alkenes are nucleophilic alkenes. Preferred $R_3$ groups include silicon or tin derivatives, such as methylene trimethyl stannyl or methylene trimethyl silyl.

Thus, the enolates of the β-hydroxy carbonyl reactions are a subset of the substituted ethylenes of this embodiment. Similar to the reaction described above for the substituted enolates, the products of this embodiment may be esters, amides, aldehydes or ketones.

In a preferred embodiment, the catalyst compounds of the invention are enantioselective; that is, they produce a single enantiomer of the β-hydroxy alkene in an enantiomeric excess.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

EXAMPLE 1

General experimental procedures

General procedures: All non-aqueous reactions were performed using oven dried glassware under an atmosphere of dry nitrogen. Diethyl ether ($Et_2O$) and tetrahydrofuran (THF) were distilled from sodium benzophenone ketyl prior to use. N,N-Diisopropylamine, dichloromethane, 1,2-dichloroethane, 2,6-lutidine, and triethylamine were distilled from calcium hydride prior to use. Toluene was distilled from sodium prior to use. Spectroscopy grade chloroform (with 0.75% ethanol) was used for all optical rotation data. Chromatographic purification of products was accomplished using forced flow chromatography on Baker 7024-R silica gel according to the method of Still (Still et al., J. Org. Chem., 43:2923 (1978)). NMR spectra were recorded on a General Electric QE Plus operating at 300 and 75 MHz for $^1H$ and $^{13}C$, respectively, and are referenced to internal solvent signals. Data for $^1H$ are reported as follows: chemical shift (δ in ppm), integration, multiplicity (s singlet, d doublet, t triplet, q quartet, dd doublet of doublets, m multiplet) and coupling constant (J in Hz). IR spectra were recorded on a Perkin-Elmer 1600 Series spectrometer. Optical rotations were determined on a JASCO DIP-ISI polarimeter operating at the sodium D line or the mercury 365 nm line and are reported as follows:

$[\alpha]^{19}_C$, or $[\alpha]^{19}_{365}$, concentration (g/100 mL), and solvent. High-resolution mass spectrometry was performed by the Midwest Center for Mass Spectrometry at the University of Nebraska, with partial support by the National Science Foundation, Biology Division (Grant No. DIR9017262).

EXAMPLE 2

Synthesis and reaction of a Tridentate Ligand Catalyst

Synthesis of tridentate ligand

The general synthesis is shown in Scheme 1, shown in FIG. 10. Amino alcohol 1 was prepared in a single stem in 46% ee following the procedure described by Smrcina et al., J. Org. Chem., 58:4534 (1993). Two successive fractional recrystallizations from benzene provided 1 in >99% ee. Condensation of 1 with 3-bromo-5-tert-butylsalicylaldehyde (2) afford the Schiff bases 3 as a crystalline solid (for a description of a large range of substituted salicylaldehydes see Larrow et al., J. Org. Chem. 59:1939 (1994)). In preliminary investigations, the catalyst prepared with 2 gave superior yields and enantioselectivities to those prepared with the tridentate ligands derived from salicylaldehydes and 5-tert-butylsalicylaldehyde. Treatment of 3 with $Ti(O^iPr)_4$ in toluene (23° C.) and subsequent evaporation of the solvent in vacuo afforded the 4 as an orange solid. Evaporation of toluene in vacuo has been reported to effect the removal of the iPrOH liberated upon complex formation of $Ti(O^iPr)_4$ with bidentate ligands such as α,α,α',α'-tetraaryl-1,3-dioxolane-4,5-dimethanols; See back et al., Helv. Chim. Acta. 75:2171 (1992) and references therein. Also, the structure of the active catalyst has not yet been determined; the illustrated structures of the Ti(IV) complexes are intended to indicate the putative catalyst composition.

Enantioselective aldol addition using the tridentate ligand

This reaction is shown in Scheme II in FIG. 11. A solution of benzaldehyde, O-trimethylsilyl O-ethyl ketene actal (5, Kita et al., J. C. S. Perkin I, 1099, (1982)), and 5 mol % 4 at 0° C. (4h) afforded a mixture of aldol products 7 and 8 in 12% and 68% yields, respectively. Conversion of 7 to the corresponding Mosher (s)-MTPA ester and analysis by $^1H$ NMR spectroscopy revealed that 7 had been formed in 78% ee (Dale et al., J. Org. Chem., 34:2543 (1969)). A similar analysis of the (S)-MTPA ester derived from 8 revealed that it had been formed in 64% ee. We interpret the isolation of carbinol 7 (12%) to be consistent with a mechanism that proceeds via intermediate 6. For such a mechanism, following the formation of 6, the $Me_3Si$ moiety is transferred to either the isopropoxide or the aldolate non-specifically.

EXAMPLE 3

Synthesis and Reaction of Pentadentate Catalyst

Synthesis of a pentadentate catalyst

The catalyst derived from 3, $Ti(O^iPr)_4$, and the commercially available 3,5-di-tert-butylsalicylic acid was subsequently examined (Scheme III, FIG. 12; see Jacobsen et al., J. Am. Chem. Soc. 113:7063 (1991)). The catalyst generated from 3, $Ti(O^iPr)_4$, and salicyclic acid gave aldol product in 85% ee, albeit in only 19% yield.

Treatment of 3 with $Ti(O^iPr)_4$ and 3,5-tert-butylsalicylic acid in toluene at 23° C. followed by solvent removal in vacuo afforded a yellow solid (9) that was freely soluble in $Et_2O$.

Synthesis of β-hydroxy carbonyls

The reaction is outlined in Scheme IV, in FIG. 13. When a solution of 5 mol % 9 in $Et_2O$ at 0° C. was treated with an aldehyde and O-trimethylsilyl O-ethyl ketene acetal (5), silylated aldol adducts were isolated in excellent yields. However, as little as 0.5 mol % may be used as well. For example, the aldol addition reaction of benzaldehyde, O-ethyl O-trimethylsilyl ketene acetal, and 5 mol % 9 afforded the silylated adduct in 94% yield. Analysis of the products was facilitated by treatment of the silyated aldolated with $Bu_4NF$ to furnish β-hydroxyl esters 10 (table 1, FIG. 14). For each adduct, preparation of the derived (S)-MPTA esters allowed the extent of asymmetric induction to be assayed by $^1H$ NMR spectroscopy. The absolute configuration of the products was established unambiguously by conversion of the known optically active diols, Parmee et al., 1991, supra. Whith the enxception of benzaldehyde, (entry 6), the observed yields and enantioselectivities exceed or match the best reported values with silyl ketene actals (Parmee et al., 1992, supra; Kiyooka et al., 1992, supra; Furuta et al., 1991, supra; Furuta et al., 1991, supra; Kiyooka et al., 1991, supra). In addition, a salient feature of this catalytic system is that the aldol addition reaction is effected with only 5 mol % catalyst. In fact, the aldol addition reaction of trans-hydrocinnamaldehyde and cinnamaldehyde with 2 mol % 9 afforded the corresponding aldol adducts with only a slight diminution in yields and ee. Moreover, slow addition of the substrates to the catalyst solution at low temperature is not necessary (see Parmee et al. 1991, supra; Kobayashi et al., 1991, supra).

The addition of 3,5-di-tert-butylsalicylic acid as a counter ion had a remarkable effect on the yields, enantioselectivity and catalytic efficiency in the asymmetric Mukaiyama addition reaction reported herein. In this regard, it is important to note that although the design of metal complexes exhibiting stronger Lewis acidity may lead to an increase in the rate of addition to aldehyde, such catalysts can have the effect of decreasing the overall rate of product formation by diminishing the rate of aldolate silylation. Thus, increasing the strength of the RCHO-Ti interaction inevitably leads to increases in the strength of the R'O-Ti bond. For strong M-0 bonds the rate of silylation of the metal aldolate might be prohibitively slow allowing a silicon-catalyzed process to compete effectively; see Carriera et al. Tetrahedron Lett. 35:4323 (1994). The salicylate chelate offers a way around this problem. We speculate that the salicylate chelate undergoes silylation in analogy to the acyloxyborane moiety in the oxazaborolidene-catalyzed aldol addition reactions (Parmee et al., 1991, supra). The metal-bound silylated salicytate may subsequently be activated by the octahedral Lewis acidic metal towards intramolecular silyl transfer to the metal aldolate.

EXAMPLE 4

Physical Data of β-hydroxy ester products

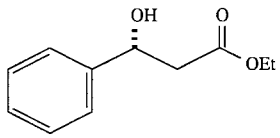

3-Hydroxy-3-phenylpropanoic acid ethyl ester.

See Maruoka et al., J. Am. Chem. Soc. 99:7705 (1977). $[\alpha]^{19}{}_{365}$ +63.1° (c=2.7, CHCl$_3$); $[\alpha]^{19}{}_C$+35.4° (c=1.6, CHCl$_3$); LR (thin film) v 3436, 3025, 3060, 2978, 2919, 1719, 1490, 1448, 1396, 1366, 1296, 1260, 1190, 1155, 1079, 1055, 1025, 949, 908, 855, 844, 756, 697; $^1$H NMR (300 MHz, CDCl$_3$) δ 1.27 (3H, t, J=7.1), 2.70 ($^1$H, dd, J=16.5, 2.3), 2.78 (1H, dd, J=16.5, 6.1), 3.27 (1H, d, J =3.4), 4.19 (2H, q, J=7.1), 5.14 (1H, m), 7.28–7.40 (5H, m); $^{13}$C (75 MHz, CDCl$_3$) δ 14.1, 43.3, 60.9, 70.3, 125.6, 127.8, 128.5, 142.4, 172.4. (S)-MTPA ester data: $^1$H NMR (CDCl$_3$) methoxy resonances at δ 3.52 and 3.42 ppm in ratio of 16.6:1 (89% ee).

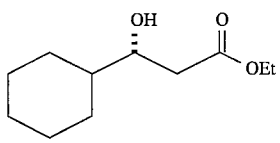

β-Hydroxycyclohexanepropionlc acid, ethyl ester.

See Bernardi et al., Tetrahedron 40:3769 (1984).

$[\alpha]^{19}{}_{365}$+20.8° (c=1.7, CHCl$_3$); $[\alpha]^{19}{}_D$+27.8° (C=0.66, CHCl$_3$); LR (thin film) v 3495, 2919, 2849, 1725, 1713, 1443, 1367, 1175, 1032, 891; $^1$H NMR (300 MHz, CDCl$_3$), δ 1.29 (3H, t, J=7.1), 1.0–1.5 (5H, m), 1.66–1.94 (6H, m), 2.45 (IH, dd, J=16.3, 9.3), 2.53 (1H, dd, J =16.3, 3.0), 3.77–3.82 (1H, m), 4.16 (2H, q, J=7.1); $^{13}$C (75 MHz, CDCl$_3$) δ 14.1, 26.0, 26.1, 26.4, 28.2, 28.7, 28.8, 38.5, 43.0, 60.6, 72.1. (S)-MTPA ester data: $^1$H NMR (CDCl$_3$) methoxy resonances at δ 3.55 and 3.52 ppm in ratio of 20.3:1 (91% ee).

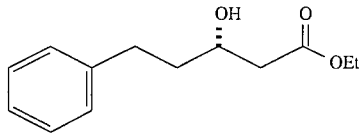

3-Hydroxy-5-phneylpentenoic acid, ethyl ester.

See Kuwujima et al. Tetrahedron Lett. 2253 (1976). $[\alpha]^{19}{}_{365}$ _3.14° (c=0.88, CNCl$_3$); $[\alpha]^{19}{}_D$+1.880° (c=1.40, CNCl$_3$); IR (thin film) v 3436,3025,2966,2919, 2860, 1725, 1495, 1448, 1372, 1302, 1255, 1184, 1155, 1084, 1025,931, 743,696; $^1$H NMR (300 MHz, CDCl$_3$) δ 1.27 (3H, t, J=7.1), 1.68–1.79 (1H, m), 1.81–1.91 (1H, m), 2.44 (1H, dd, J=16.5, 8.4), 2.52 (1H, dd, J=16.5, 3.7), 2.65–2.78 (1H, m), 2.80–2.88 (1H, m), 3.10 (1H, s), 4.02 (1H, m), 4.17 (2H, q, J=7.1), 7.16–7.36 (5H, m); $^{13}$C (75 MHz, CDCl$_3$) δ 14.1, 31.7, 38.1, 41.2, 60.7, 67.2, 125.9, 128.4, 128.4, 141.7, 173.0. (S)-MTPA ester data: $^1$H NMR (CDCl$_3$) methoxy resonances at δ 3.57 and 3.54 ppm in ratio of 14.0: I (87% ee).

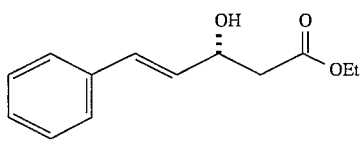

3-Hydroxy-5-phenyl-4-pentenoic acid, ethyl ester. See Araki, S.; Ito, H.; Busugan, Y. Syn. Commun. 1988,453. $[\alpha]^{19}{}_{365}$ +27.6° (c–0.94, CHCl$_3$); $[\alpha]^{19}{}_D$ +13.6° (c=1.2, CHCl$_3$); IP (thin film() v 3424, 2978, 1954, 1883, 1725, 1713, 1601, 1578, 1496, 1449, 1373, 1155, 1102, 1032, 967, 750, 691; $^1$H NMR (300 MHz, CDCl$_3$) δ 1.30 (3H, t, J=7.1), 2.61 (1H, dd, J=16.3,5.9), 2.69 (1H, dd, J=16.3,4.1), 3.10 ($^1$H, d, J=4.2), 4.21 (2H, q, J=7.1), 4.75 (1H, m), 6.23 (1H, dd, J –16.0,6.1), 6.68 (1H, d, J=16.0), 7.246–7.42 (5H, m); $^{13}$C (75 MHz, CDCl$_3$) δ 14.3, 41.8, 60.9, 69.0, 126.6, 127.9, 128.7, 130.2, 130.7, 136.6, 172.2. (S)-MTPA ester data: $^1$H NMR (CDCl$_3$) methoxy resonances at δ 3.58 and 3.52 ppm in ratio of 18.4:1 (90% ee).

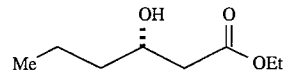

3-Hydroxyhexanoic acid, ethyl ester.

See Crump, D. R. Aus. J. Chem 1982, 1945. $[\alpha]^{19}{}_{365}$+ 10.5° (c=0.58, CNCl$_3$); $[\alpha]^{19}{}_D$+9.46° (c=0.83, CHCl$_3$); IR (thin film) v 3483, 2955, 2919, 2861, 1725, 1708, 1449, 1367, 1302, 1290, 1179, 1138, 1079, 1014, 955, 850, 720, 685; $^1$H NMR (300 MHz, CDCl$_3$) δ 0.93 (3H, t, J=7.1), 1.27 (3H, t, J=7.1), 1.34–1.55 (2H, m), 2.39 (1H, dd, J=16.5, 8.9), 2.50 (1H, dd, J=16.5,3.2), 2.94 (1H, d, J=4.0), 4.02 (1H, m), 4.17 (2N, q, J=7.1); $^{13}$C (75 MHz, CDCl$_3$) δ 13.9, 14.2, 18.7, 38.6, 41.3, 60.6, 67.7, 173.1. (S)-MTPA ester data: $^1$H NMR (C$_6$D$_6$) methoxy resonances at δ 3.50 and 3.43 ppm in ratio of 13.1:1 (86% ee).

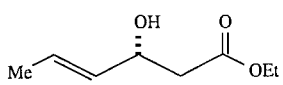

3-Hydroxy-4-hexenoic acid, ethyl ester.

See Zibuch, R.; Streiber, J. M. J. Org. Chem. 1989,54, 4717. [α]$^{19}_{365+26.5°}$ (c=1.00, CHCl$_3$); [α]$^{19}_D$+11.3° (c=1.00, CNCl$_3$0; IR (thin film) v 3436, 2978, 2919, 1713, 1443, 1366, 1302, 1278, 1249, 1167, 1114, 1091, 1026, 961; $^1$H NMR (300 MHz, CDCl$_3$) δ 1.27 (3H, t, J=7.1), 1.69 (3H, dd, 'I,,=6.3, 0.8), 2.48 (1H, dd, J =16.4, 2.4), 2.55 (1H, d, J=16.4,4.1), 2.86 (1J, d, J=4.0), 4.17 (2H, q, J=7.1), 4.48 (1H, m), 5.51 (1J, m), 5.73 (1H, m); $^{13}$C (75 MHz, CDCl$_3$) δ 14.2, 17.7, 41.5, 60.7, 68.9, 127.5, 131.7, 172.4. (S)-MTPA ester data: $^1$H NMR (C$_6$D$_6$) methoxy resonances at δ 3.50 and 3.44 ppm in ratio of 22.0:1 (91% ee).

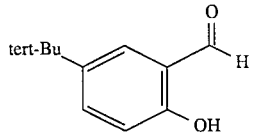

5-tert-Butylsalicylaldehyde.

See Ken et al., J. Chem. Soc. Perkin Trans. 1, 1990, 887; Craig et al., Inorg. Chem. 1989,28, 2082. Formylation of 4-tert-butylphenol was carried out according to the procedure of Jacobsen, J. Org. Chem., 1992,57,4320: bp=109.5° C. (4 mmHg); IR (thin film) v 3178, 3072, 2955, 2861, 1696, 1655, 1619, 1584, 1478, 1390, 1373, 1361, 1314, 1284, 1261, 1226, 1179, 926, 826, 773, 732, 650, 603; $^1$H NMR (C$_6$D$_6$): δ 1.09 (9H, s), 6.84 (1H, d, J=8.8), 6.97 (1H, d, J=2.5), 7.10 (1H, dd, J=8.8,2.5), 9.22 (1H, s), 11:42 ($^1$H, s); $^{13}$C NMR (C$_6$D$_6$): δ 31.2, 33.9, 117.5, 120.4, 129.8, 134.5, 142.3, 60.1, 196.8.

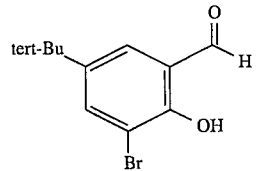

Bromination of 5-tert-Butylsalicylaldehyde.

See Werner, Bull. Soc. Chim. Fr. 46:277 (1886). 5-tert-Butylsalicylaldehyde (1.00 g, 5.61 mmol) was dissolved in 15 glacial acetic acid. To the solution was added bromine (360 μL, 7.01 mmol) dropwise. The dark yellow solution was allowed to stir for 24 h at 23° C. The solution was then diluted with 10 mL water to precipitate the product. The crystals were collected by suction Filtration and recrystallized from 4:1 ethanol/water to give needles: mp=81° C.; 1R (thin film) v 3072, 3037, 2955, 2861, 2731, 1661, 1614, 1455, 1414, 1378, 1325, 1261, 1214, 1155, 1114, 1014, 938, 885, 850, 814,732,691, 626; $^1$H NMR (C$_6$D$_6$): δ 0.98 (9H, s), 6.79 (1H, d, J=2.3), 7.65 (1H, d, J=2.3), 8.96 (1H, s), 11.77 (1H, s); $^{13}$C NMP (C$_6$D$_6$): δ 30.9, 33.9, 111.3, 120.9, 129.3, 137.3, 143.6, 156.5, 196.1; HRMS (EI): calcd for C$_{11}$H$_{13}^{79}$BrO$_2$ (M—H) $^+$255.0021, found.

General Procedure for Schiff Base Formation.

(R)-2-Amino-2'-hydroxy 1,1'binaphthyl (0.100 g, 0.350 mmol) and 1.2 eq of the salicylaldehyde (0.420 mmol) were taken up in 5 mL absolute ethanol and heated to reflux for 24 h. The solvent was removed in vacuo and the product was isolated by chromatography on silica gel using 6:1 hexane/ EtOAc. The orange-product was dissolved in 10 mL CN$_2$Cl$_2$ and washed with a 5% solution of aqueous NaNCO$_3$. After drying the organic phase over anhydrous Na$_2$SO$_4$, the solvent was removed in vacuo and the resulting orange powder was dried under vacuum (2 mm Hg) over 8 h.

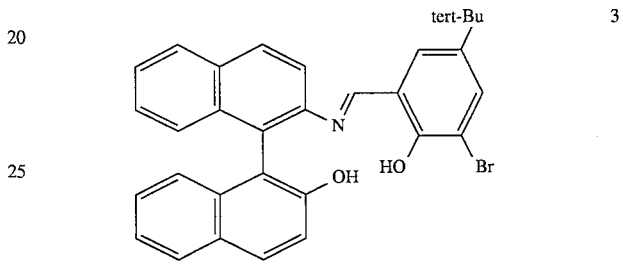

3: (from Scheme I) mp=164.20 C.; [α]$^{19}_D$+22.8° (c=1.00, CNCl$_3$); IR (thin film) v 3389, 3049, 2955, 2908, 2861, 1608, 1502, 1461, 1425, 1343, 1261, 1208, 1161, 1138, 1067, 973, 950, 926, 873, 808, 744, 714; $^1$H NMR (300 MHz, DMSO-d$_6$) δ 1.22 (9H, s), 6.79 (1H, d, J=7.7), 7.10 (1H, d, J=8.4), 7.13 (1H, dd, J=8.4, 7.7), 7.22 (1J, dd, J=7.7, 7.0), 7.31 (1J, dd, 7.7, 7.7), 7.37 (1J, d, 8.9), 7.48 (1H, dd, 7.7, 7.0), 7.54 (1H, s), 7.61 (1H, s), 7.87 (1H, d, J=7.7), 7.90 (1H, d, J=9.2), 7.93 (1H, d, J=9.2), 8.04 (1H, d, J=7.7), 8.16 (1H, d, J=8.9), 9.07 (1H, s), 9.59 (1H, s), 13.21 (1H, s); $^{13}$C (75 MHz, DMSO-d$_6$) δ 31.0, 33.9, 109.5, 115.4, 117.8, 118.4, 119.5, 122.5, 123.8, 125.9, 126.1, 126.3, 126.8, 127.9, 128.1, 128.2, 129.0, 129.1 129.3, 129.5, 132.4, 133.0, 133.1, 133.6, 142.3, 143.1, 152.8, 154.8, 162.8; HRMS (EI): calcd for C$_{31}$H$_{26}^{79}$BrNO$_2$(M—H)+522.1069, found. mp=148° C.; [α]$^{19}_c$+83.2° (c=1,00, CHCl$_3$); IR (thin film) v 3366,3049,2943, 2861, 2355, 1619, 1572, 1484, 1461, 1425, 1373, 1355, 1337, 1284, 1261, 1202, 1173, 1138, 1067, 1020, 973, 920, 867, 814, 744; $^1$H NMR (300 MHz, CDCl$_3$) δ 1.22 (9H, s), 4.87 (1H, s), 6.86 (1H, d, J=8.0), 7.01 (1H, d, J=8.2), 7.21 (1H, dd, J=8.0,7.0), 7.21 (1H, d, J=8.0), 7.31 (1H, dd, J=8.0,7.0), 7.36 (1H, s), 7.36 (1H, dd, J=8.0, 7.0), 7.37 (1H, d, J=8.9), 7.50 (1H, d, J=8.2), 7.51 (1H, t, J=8.0, 7.0), 7.68 (1H, d, J=8.9), 7.88 (1H, d, J=8.0), 7.96 (1H, d, J=8.8), 7.98 (1H, d, J=8.0), 8.12 (1H, d, J=8.8), 8.69 (1H, s), 11.9 (1H, s); $^{13}$C (75 MHz, DMSO-d$_6$) δ 30.7, 34.7, 113.3, I 15.9, 116.1, 116.9, 117.4, 118.3, 122.4, 123.8, 125.6, 126.1, 126.2, 126.6, 127.9, 128.1, 128.1, 128.9, 129.1, 129.3, 132.2, 132.3, 133.1, 133.6, 143.5, 152.7, 156.5, 160.0, 161.8; HRMS (EI): calcd for C$_{31}$H$_{27}$NO$_2$(M–H)+ 444.1964, found.

EXAMPLE 5

Synthesis using 2-Methoxypropene

A comparison of the silyl enol ethers and alkyl enol ethers as reactants is shown below in scheme 3:

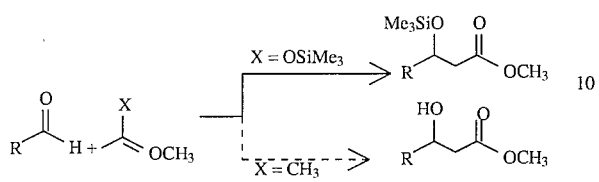

When hydrocinnamaldehyde and 2-methoxypropene were dissolved in toulene or ether with 5 mol % of catalyst, no additon product was isolated at 23° C., in contrast to the reaction with silyl ketene acetals. This lack of reactivity is consistent with the attenuated nucleophilicity of 2-methoxypropene relative to the silyl compounds. However, these rate differences could be compensated by using 2-methoxypropene as the solvent. Accordingly, the aldol addition reaction was conducted by dissolution of the catalyst (2–10 mol %) in 2-methoxypropene (filtered through Activity 1 basic alumina, followed by distillation) at 0° C. followed by addition of 2,6-di-tert-butyl-4-methylpyridine (0.4 equiv) and the aldehydes shown in Table 1, below. The addition reactions in the absence of added base gives good yields and selectivities; however, because of the sensitivity of the solvent 2-methoxypropene and the reaction products to decomposition in the presence of adventitious H+, a hindered base as an H+ scavenger was employed. The addition of $Et_3N$, $^iPr_2NEt$, or 2,6-lutidine leads to diminution of the reaction rate.

After stirring for 1.5 to 22 hours at 0°–23° C. the reaction mixture was concentrated in vacuo and the residue treated with a biphasic mixture of $ET_2O$ and aqueous 2N HCl solution to afford the corresponding β-hydroxyketone adduct after work-up and chromatography on silica gel.

TABLE 1

| Catalytic Asymmetric Aldol Additions 2-methoxypropene | | | | |
| --- | --- | --- | --- | --- |
| Entry | Aldehyde | Temp. | Yield | ee[a,b] |
| 1 | Ph(CH$_2$)$_3$—≡—CHO | 0° C. | 99% | 98% |
| 2 | TBSOCH$_2$—≡—CHO | 0° C. | 85%[c] | 93% |
| 3 | Ph—≡—CHO | 0° C. | 99% | 91% |
| 4 | Ph∼∼CHO | 0–23° C. | 98% | 90% |
| 5 | PhCHO | 0–23° C. | 83% | 66% |
| 6 | c-C$_6$H$_{11}$CHO | 0–23° C. | 79% | 75% | a) For each entry, the ee was determined by preparation of the derived (S)-MPTA ester, analysis by $^1$H NMR spectroscopy, and comparison with authentic racemic material. b) The absolute configuration of the aldol adducts was established in the following manner: Entry 3, the (S)-MPTA ester was hydrogenated to the corresponding saturated ester and compared to the known (S)-MPTA esters of the adduct of Entry 4; Entries 4–6, comparison to the known compounds; entries 1–2, by analogy to the product of entry 3. c) The adduct was treated with a solution of TFA/THF instead of $Et_2O/2N$ HCl.

We claim:

1. A compound having the formula:

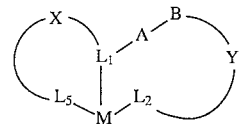

wherein

M is selected from the group consisting of Fe, Ni, Cu, Sc, Y, La, Ti, Zr, and Hf;

$L_1$, $L_2$, and $L_5$=are each selected from the group consisting of O, N, S and P;

A is either a single or a double bond;

B is selected from the group consisting of C, N, S and P;

X is substituted biphenyl or substituted or unsubstituted: binaphthyl or bisphenanthrol; and Y is substituted phenyl, substituted naphthyl, or substituted biphenyl.

2. A compound having the formula:

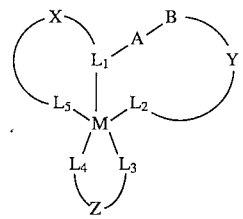

wherein

M is selected from the group consisting of Fe, Ni, Cu, Sc, Y, La, Ti, Zr, and Hf;

$L_1$, $L_2$, $L_3$, $L_4$ and $L_5$=are each selected from the group consisting of O, N, S and P;

A is either a single or a double bond;

B is selected from the group consisting of C, N, S and P;

X is substituted biphenyl or substituted or unsubstituted: binaphthyl or bisphenanthrol;

Y is substituted phenyl, substituted naphthyl, or substituted biphenyl; and

Z is substituted or unsubstituted phenyl, biphenyl, or diphenyl-methane.

3. A compound having the formula:

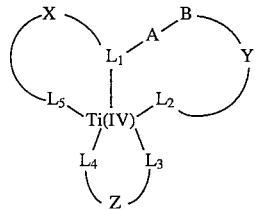

wherein:

$L_1$ is nitrogen;

$L_2$, $L_3$, $L_4$ and $L_5$ are each oxygen;

A is either a single or a double bond;

B is selected from the group consisting of C, H, S and P;

X is substituted biphenyl or substituted or unsubstituted: binaphthyl or bisphenanthrol;

Y is substituted phenyl, substituted naphthyl, or substituted biphenyl; and

Z is substituted or unsubstituted phenyl, biphenyl, or diphenyl-methane.

4. The composition according to claim 3 wherein said compound is an enantioselective catalyst for the production of β-hydroxy carbonyl compounds.

5. A compound having the formula:

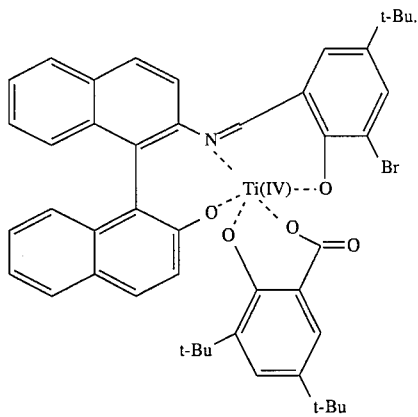

6. A compound according to claim 2 wherein "Y" has the formula:

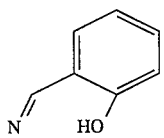

7. A compound according to claim 2 wherein "Y" has the, formula:

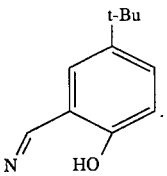

8. A compound according to claim 2 wherein "Y" has the formula:

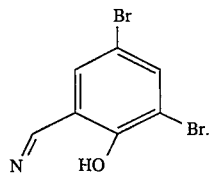

9. A compound according to claim 2 wherein "Y" has the formula:

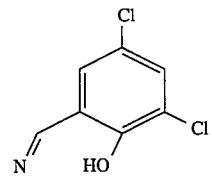

10. A compound according to claim 2 wherein "Y" has the formula:

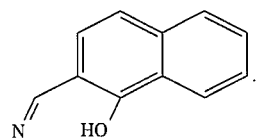

11. A compound according to claim 2 wherein "Y" has the formula:

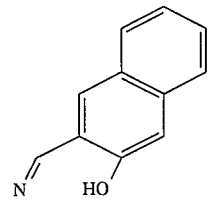

12. A compound according to claim 2 wherein "Z" has the formula:

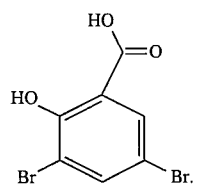

13. A compound according to claim 2 wherein "Z" has the formula:

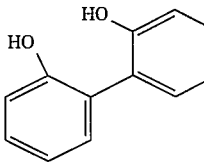

14. A composition comprising a compound according to claim 1, 2, 3 or 5 and a substituted enolate.

15. A composition according to claim 14 further comprising an aidehyde.

16. A composition according to claim 14 further comprising a ketone.

17. A composition according to claim 14 wherein said substituted enolate is a silyl enol ether.

18. A composition according to claim 14 wherein said substituted enolate is an alkyl enol ether.

19. A composition according to claim 14 wherein said substituted enolate is 2-methoxypropene.

20. A method for making β-hydroxy carbonyl compounds comprising contacting an aldehyde and a substituted enolate with a compound having the formula:

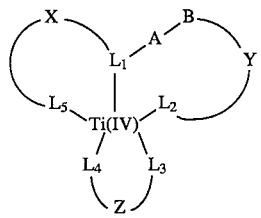

wherein:

$L_1$ is nitrogen;

$L_2$, $L_3$, $L_4$ and $L_5$ are each oxygen;

A is either a single or a double bond;

B is selected from the group consisting of C, N, S and P;

X is substituted biphenyl or substituted or unsubstituted: binaphthyl or bisphenanthrol;

Y is substituted phenyl, substituted naphthyl, or substituted biphenyl; and

Z is substituted or unsubstituted phenyl, biphenyl, or diphenyl-methane.

21. The method according to claim 20 wherein said compound has the formula:

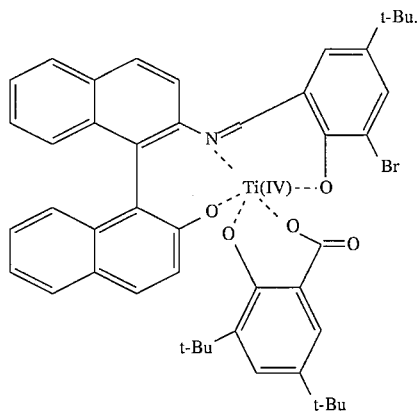

22. The method according to claim 20 wherein said β-hydroxy carbonyl compound is produced in enantiomeric excess.

23. A method for making β-hydroxy carbonyl compounds comprising contacting an aldehyde and a substituted enolate with a compound having the formula:

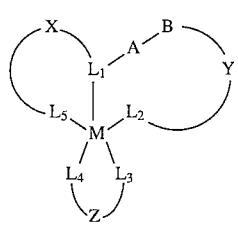

wherein

M is selected from the group consisting of Fe, Ni, Cu, Sc, Y, La, Ti, Zr, and Hf;

$L_1$, $L_2$, $L_3$, $L_4$ and $L_5$=are each selected from the group consisting of O, N, S and P;

A is either a single or a double bond;

B is selected from the group consisting of C, N, S and P;

X is substituted biphenyl or substituted or unsubstituted: binaphthyl or bisphenanthrol;

Y is substituted phenyl, substituted naphthyl, or substituted biphenyl; and

Z is substituted or unsubstituted phenyl, biphenyl, or diphenyl-methane.

24. A method according to claim 20, 21 or 23 wherein said substituted enolate is a silyl enol ether.

25. A method according to claim 20, 21, or 23 wherein said substituted enolate is an alkyl enol ether.

26. A method according to claim 20, 21, or 23 wherein said substituted enolate is 2-methoxypropene.

27. A method according to claim 20, 21 or 23 wherein said β-hydroxy carbonyl compound is selected from the groups consisting of β-hydroxy amides, β-hydroxy esters, β-hydroxy thioesters, β-hydroxy ketones, or β-hydroxy aldehydes.

* * * * *